United States Patent
Gruhne et al.

(10) Patent No.: US 11,119,109 B2
(45) Date of Patent: Sep. 14, 2021

(54) METHOD FOR DETECTING BASOPHIL ACTIVATION

(71) Applicant: EUROIMMUN MEDIZINISCHE LABORDIAGNOSTIKA AG, Luebeck (DE)

(72) Inventors: Julia Gruhne, Hamburg (DE); Henning Seismann, Nienwohld (DE); Alf Weimann, Luebeck (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 171 days.

(21) Appl. No.: 16/055,936

(22) Filed: Aug. 6, 2018

(65) Prior Publication Data

US 2019/0049461 A1 Feb. 14, 2019

(30) Foreign Application Priority Data

Aug. 8, 2017 (EP) .................................... 17001352
Dec. 5, 2017 (EP) .................................... 17001979

(51) Int. Cl.
*G01N 33/68* (2006.01)
*G01N 33/50* (2006.01)
*G01N 33/569* (2006.01)

(52) U.S. Cl.
CPC ..... *G01N 33/6869* (2013.01); *G01N 33/5047* (2013.01); *G01N 33/5091* (2013.01); *G01N 33/5094* (2013.01); *G01N 33/56972* (2013.01); *G01N 2800/24* (2013.01)

(58) Field of Classification Search
CPC ......... G01N 33/6869; G01N 33/56972; G01N 33/5094; G01N 2800/24; G01N 21/76; G01N 33/577
See application file for complete search history.

(56) References Cited

U.S. PATENT DOCUMENTS

| 4,435,509 | A | 3/1984 | Berthold et al. | |
|---|---|---|---|---|
| 2009/0246805 | A1 | 10/2009 | Moriyama et al. | |
| 2010/0167317 | A1* | 7/2010 | Daeron ................ | C12N 5/0642 435/7.24 |
| 2015/0299315 | A1* | 10/2015 | Chronopoulou ....... | C07K 16/28 435/7.24 |
| 2016/0227640 | A1 | 8/2016 | Laurisch et al. | |

FOREIGN PATENT DOCUMENTS

| DE | 102 35 310 | A1 | 2/2004 |
|---|---|---|---|
| EP | 2 037 269 | A1 | 3/2009 |
| EP | 3 196 209 | A1 | 7/2017 |
| EP | 3 244 212 | A1 | 11/2017 |
| WO | 98/32014 | A1 | 7/1998 |
| WO | 2012/028167 | A2 | 3/2012 |
| WO | 2012/044756 | A2 | 4/2012 |

OTHER PUBLICATIONS

Smaniotto et al. (PLOSone 2013 vol. 8, e70292) (Year: 2013).*
Shiono et al. (J. Sep Sci. 2016 vol. 39, p. 3062-3071) (Year: 2016).*
Rose et al. (J. Allery Clin. Immun. 2017 vol. 139, Abstract#392). (Year: 2017).*
Valent et al. (Methods 2004 32:265-270) (Year: 2004).*
Kricka (Analytical Achimica Acta 2003 500:279-286) (Year: 2003).*
Hoffmann et al. (European J Allergy and Clinical Imunology 2015, 70, p. 1393-1405). (Year: 2015).*
Mahfouz et al. "Evaluation of chemiluminescence and flow cytometry as tools in assessing production of hydrogen peroxide and superoxide anion in human spermatozoa" Fertility and Sterility 2009 92:819 (Year: 2009).*

(Continued)

*Primary Examiner* — Changhwa J Cheu
(74) *Attorney, Agent, or Firm* — Grüneberg and Myers PLLC

(57) ABSTRACT

The present invention relates to a method for diagnosing an allergy, comprising the steps of bringing into contact of basophils from a whole blood sample of a patient with an allergen in an aqueous solution in the presence of whole blood, with a volume content of whole blood in the aqueous solution of at least 20 percent by volume, under conditions that allow activation of the basophils by the allergen, enrichment of the basophils from step a) and detection of activated basophils, wherein the detection is carried out in that the expression of a marker characteristic of activated basophils is detected by means of chemiluminescence; and a kit comprising a vessel for bringing the basophils into contact with the allergen, wherein the vessel is preferably a microtiter plate, optionally an allergen, an agent for detecting a marker characteristic of activated basophils by means of chemiluminescence, wherein the agent is preferably a ligand against the marker provided with a label capable of chemiluminescence and the ligand more preferably is a monoclonal antibody, optionally an agent for stopping activation of the basophils, an optionally immobilizable ligand that binds to a polypeptide located on the cell surface of basophils independently of its activation state, wherein the ligand is preferably a monoclonal antibody against the polypeptide, and optionally an agent for lysing and/or removing erythrocytes.

19 Claims, 26 Drawing Sheets

(56) References Cited

OTHER PUBLICATIONS

Santos et al. Basophil activation test: food challenge in a test tube or specialist research tool? Clin. Transl. Allergy 2016 6:10 (Year: 2016).*
European Office Action dated Sep. 16, 2019 for corresponding EP Application No. 18 187 647.5 (with English translation) (5 pages).
Agis et al., "Comparative immunophenotypic analysis of human mast cells, blood basophils and monocytes," *Immunology* 87(4):535-543, 1996.
Balzer et al., "Basophil Activation Test Using Recombinant Allergens: Highly Specific Diagnostic Method Complementing Routine Tests in Wasp Venom Allergy," *Plos One* 9(10):e108619, 2014. (9 pages).
Blank et al., "Identification, Recombinant Expression, and Characterization of the 100 kDa High Molecular Weight Hymenoptera Venom Allergens Api m 5 and Ves v 3," *J. Immunol.* 184(9):5403-5413, 2010. (12 pages).
Extended European Search Report, dated Oct. 16, 2017, for European Application No. 17001352.8-1408. (German Version Only) (10 Pages).
Glycotope Biotechnology, "Instructions BASOTEST," Version May 2012, 2016, 8 pages.
Joulia et al., "Direct monitoring of basophil degranulation by using avidin-based probes," *J. Allergy Clin. Immunol.* 140(4):1159-1162, 2017. (10 pages).
Kepley et al., "Identification and Partial Characterization of a Unique Marker for Human Basophils," *J. Immunol.* 154(12):6548-6555, 1995.
Knol et al., "Monitoring human basophil activation via CD63 monoclonal antibody 435," *J. Allergy Clin. Immunol.* 88(3 Pt. 1):328-338, 1991.
Mochizuki et al., "The release of basogranulin in response to IgE-dependent and IgE-independent stimuli: Validity of basogranulin measurement as an indicator of basophil activation," *J. Allergy Clin. Immunol.* 112(1):102-108, 2003.
Saarne et al., "Rational design of hypoallergens applied to the major cat allergen Fel d 1," *Clin. Exp. Allergy* 35(5):657-663, 2005.
Sainte-Laudy et al., "Analysis of anti-IgE and allergen induced human basophil activation by flow cytometry. Comparison with histamine release," *Inflamm. Res.* 47(10):401-408, 1998.
Seismann et al., "Recombinant phospholipase A1 (Ves v 1) from yellow jacket venom for improved diagnosis of hymenoptera venom hypersensitivity," *Clin. Mol. Allergy* 8(7), 2010. (8 pages).

* cited by examiner

FIG. 3E
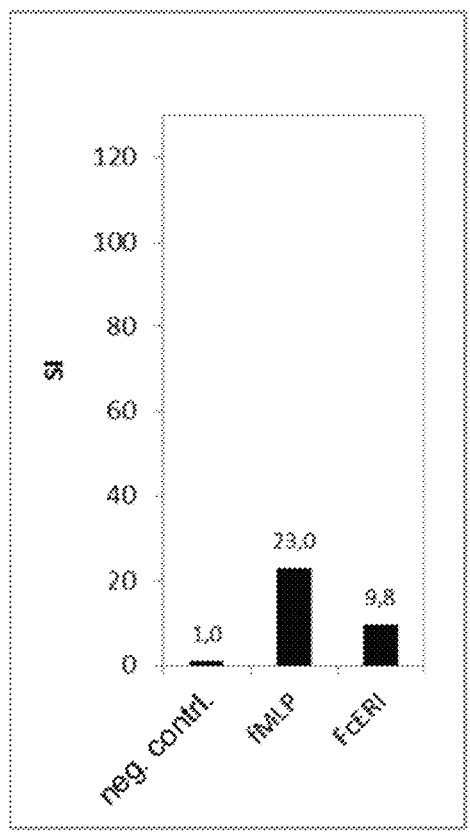
FIG. 3F
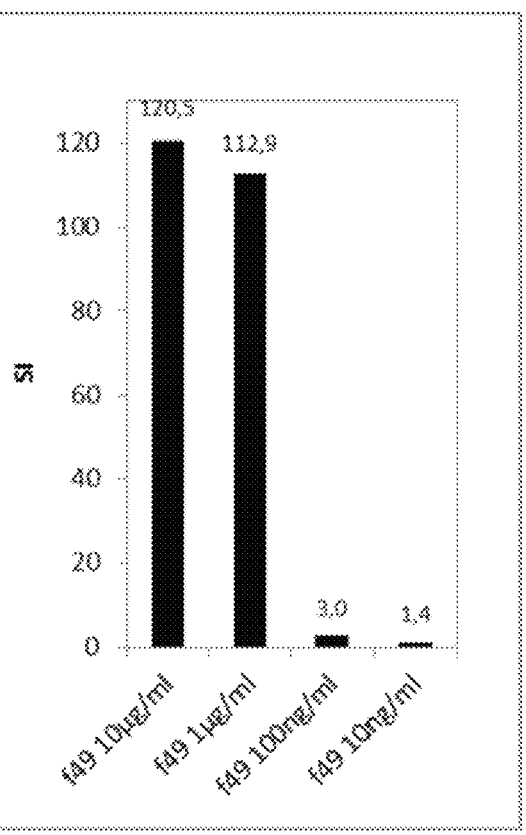
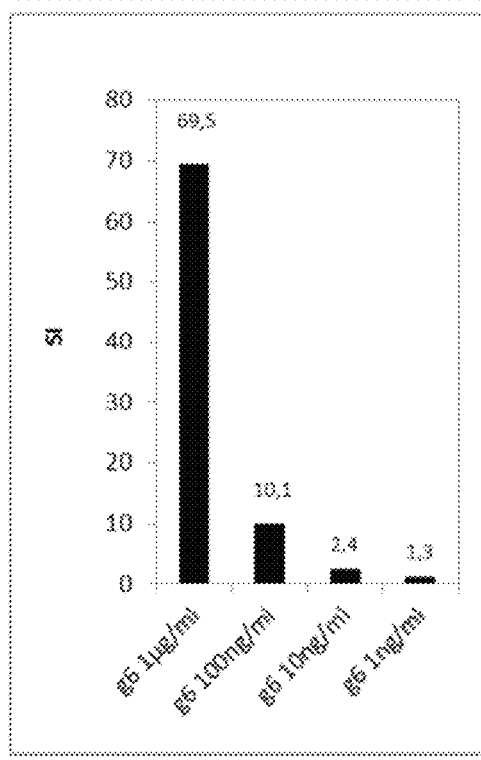
FIG. 3G
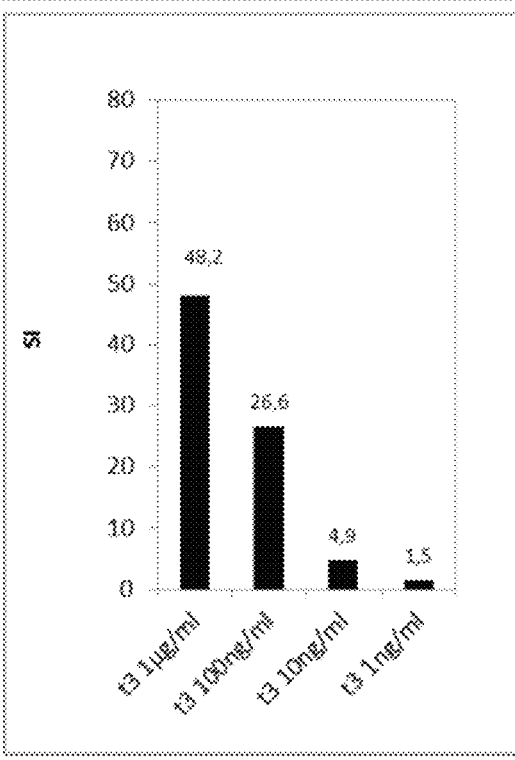
FIG. 3H

FIG. 4E 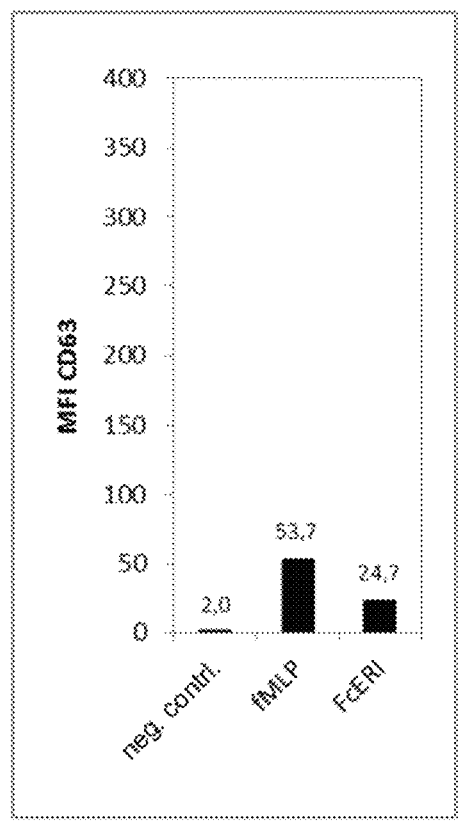 FIG. 4F 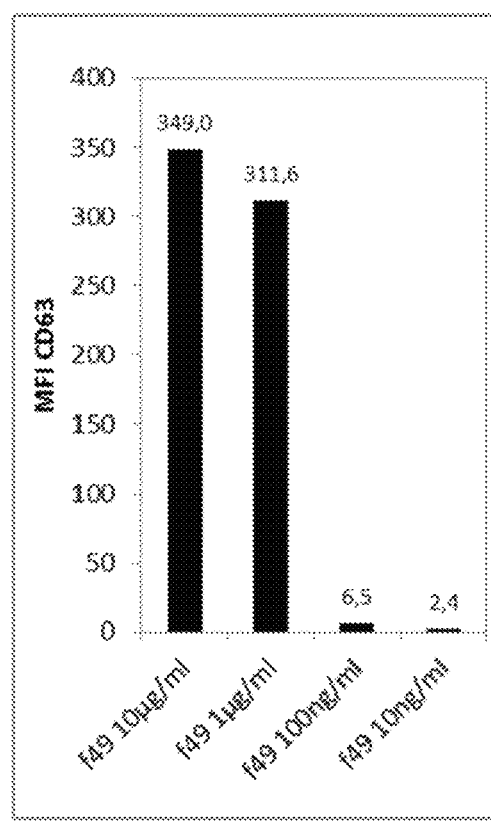
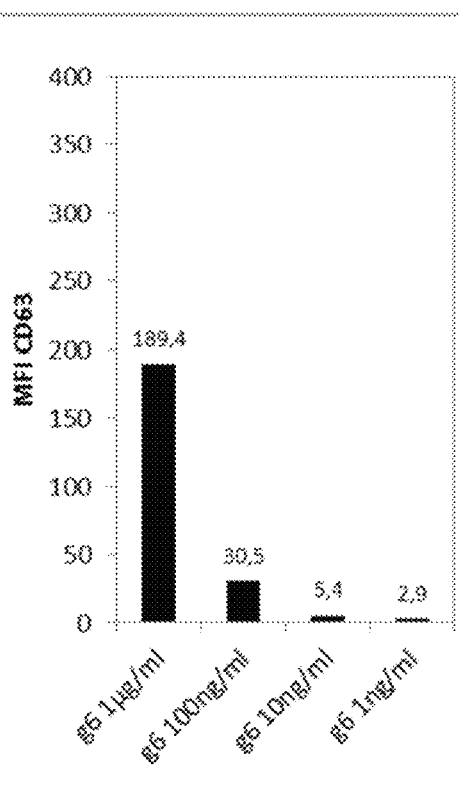 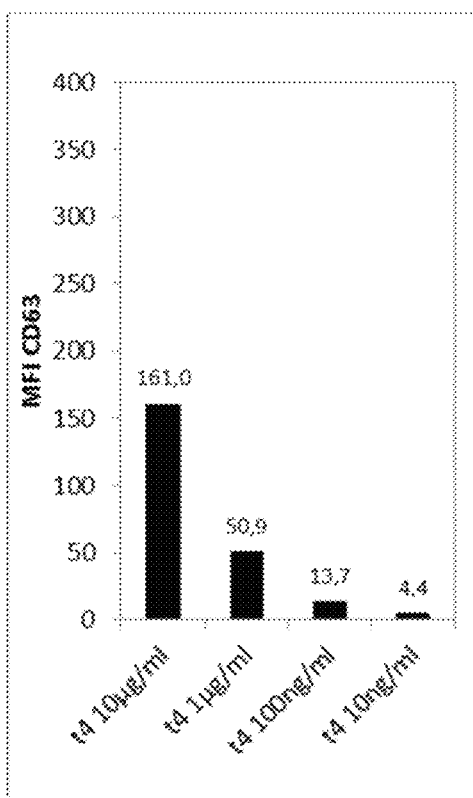
FIG. 4G FIG. 4H

FIG. 6E
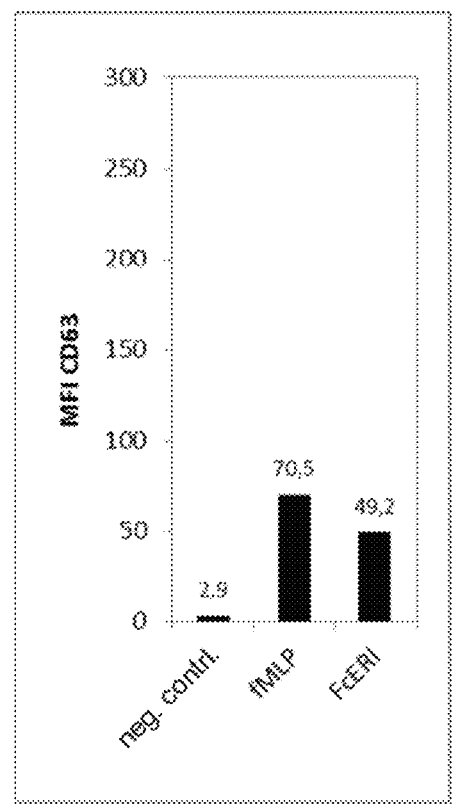
FIG. 6F
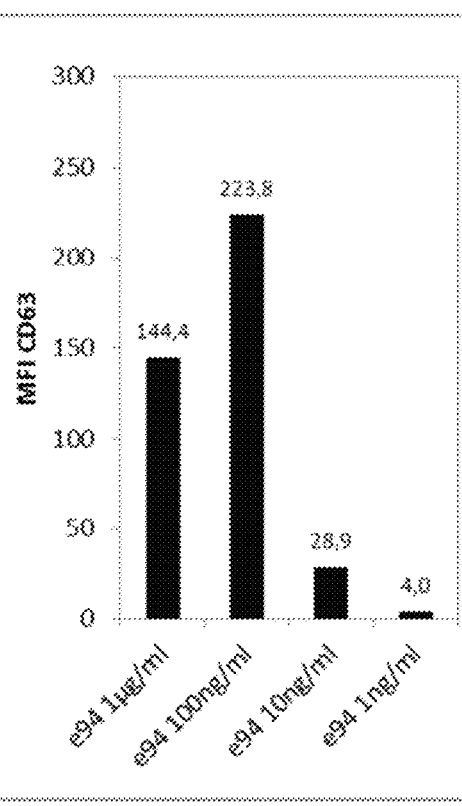
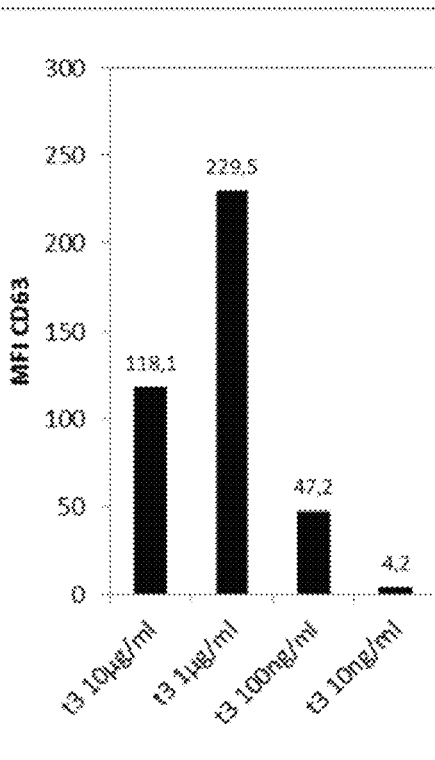
FIG. 6G
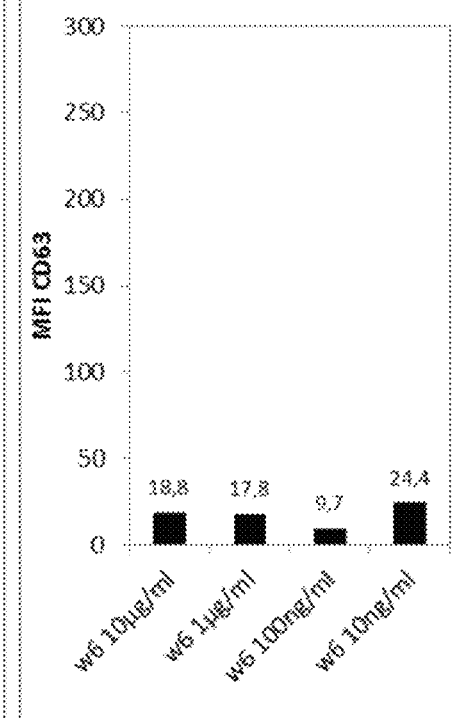
FIG. 6H

FIG. 7C                    FIG. 7D

FIG. 8E
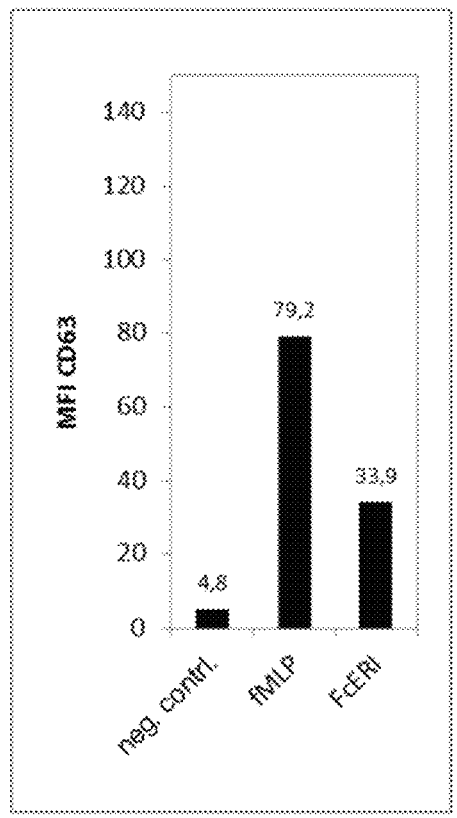
FIG. 8F
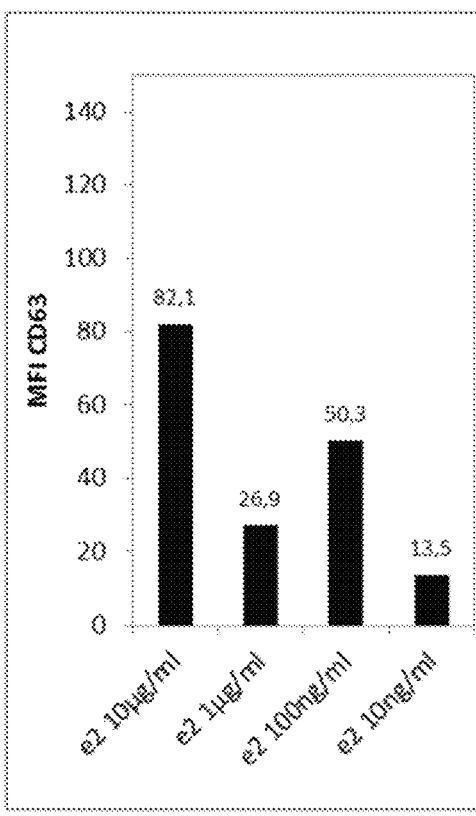
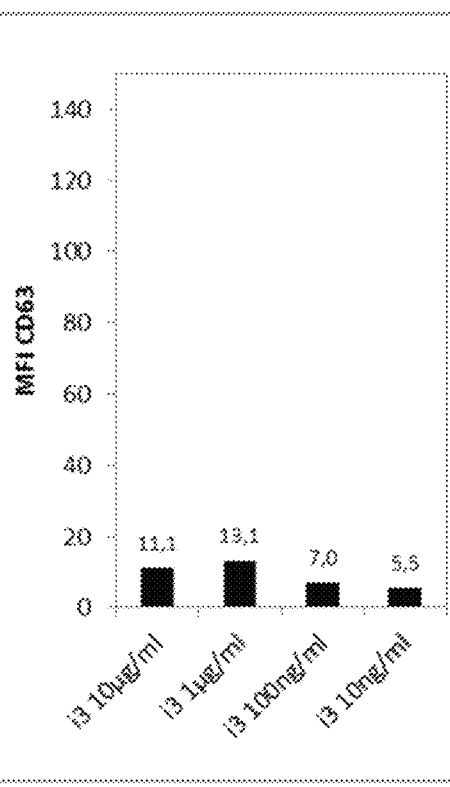
FIG. 8G
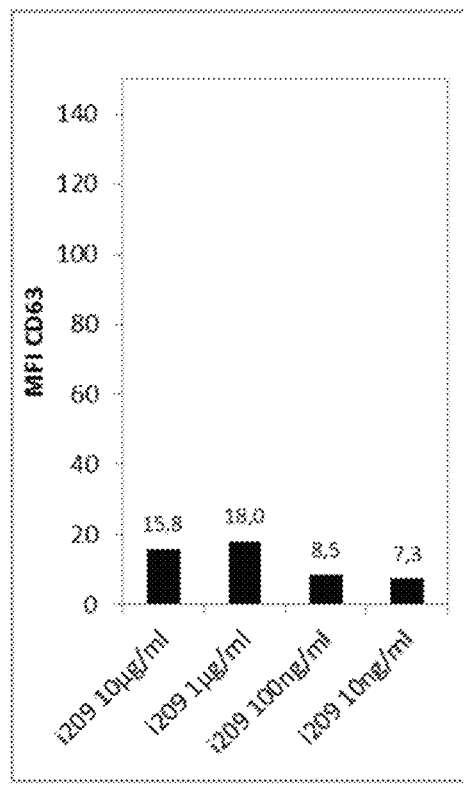
FIG. 8H

FIG. 9E
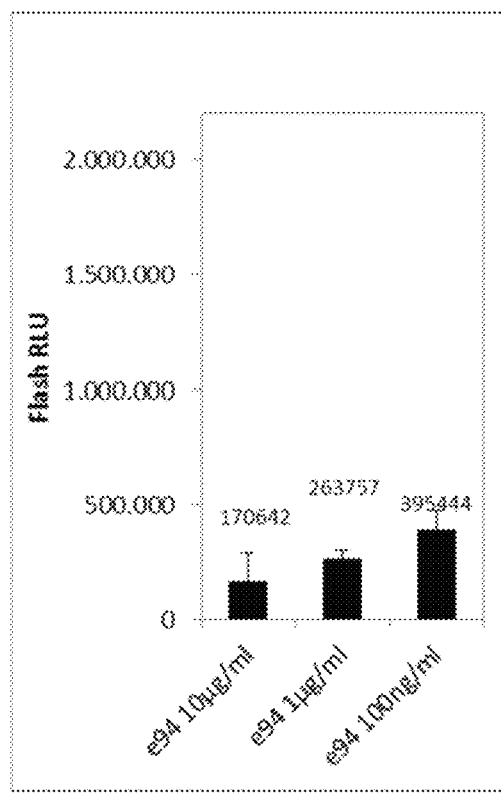
FIG. 9F
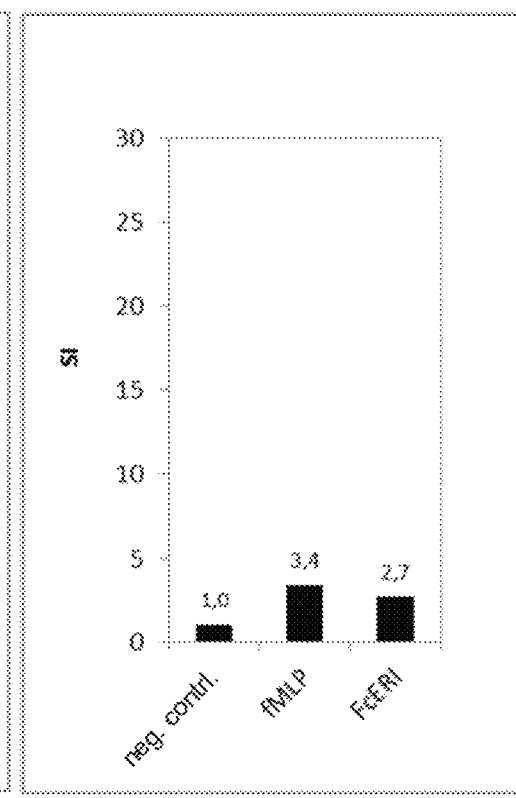
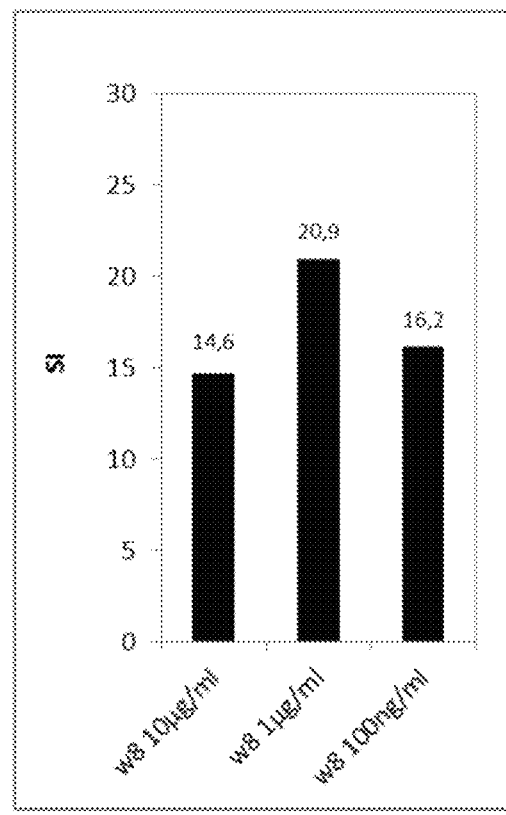
FIG. 9G
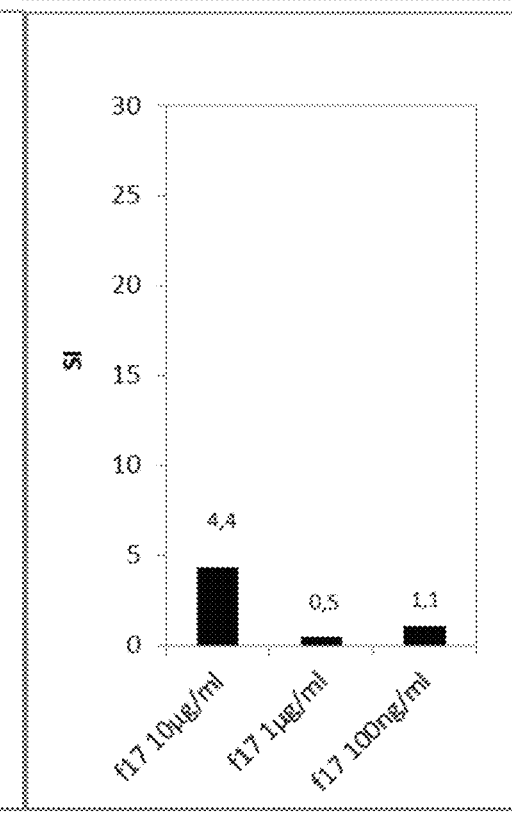
FIG. 9H

FIG. 10E
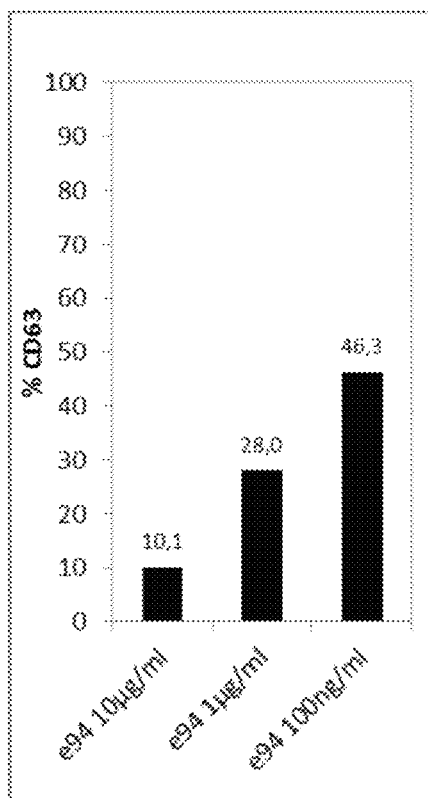
FIG. 10F
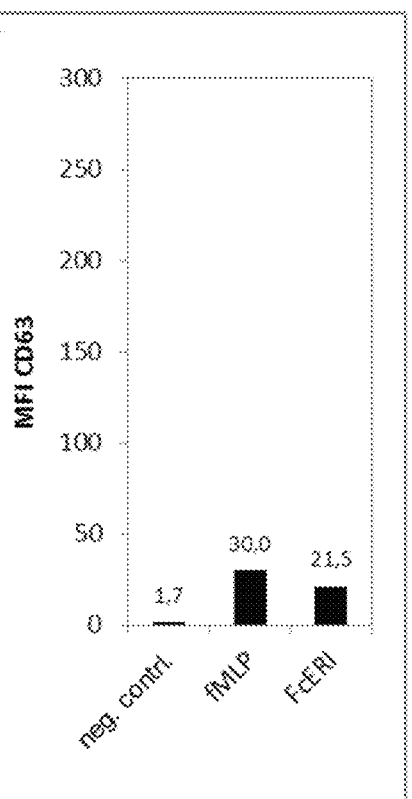
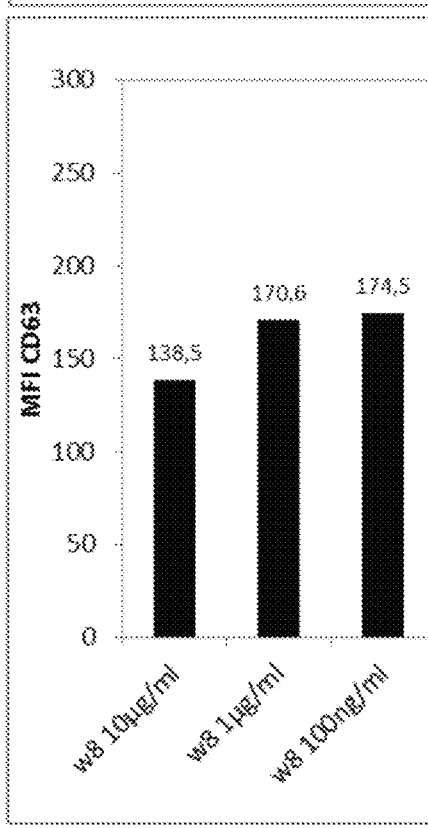
FIG. 10G
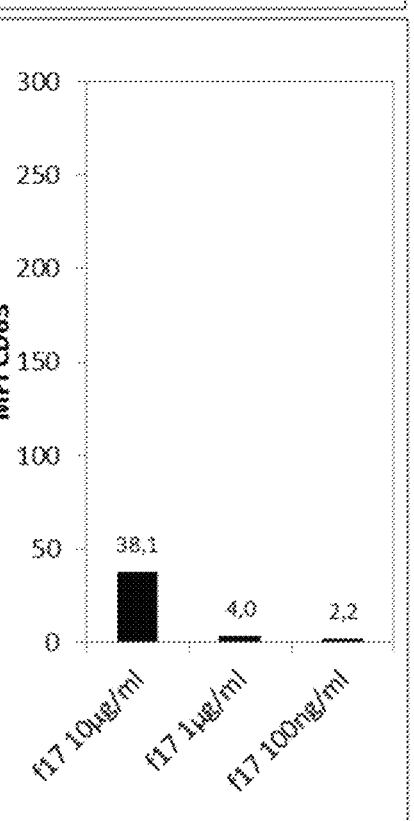
FIG. 10H

FIG. 12A
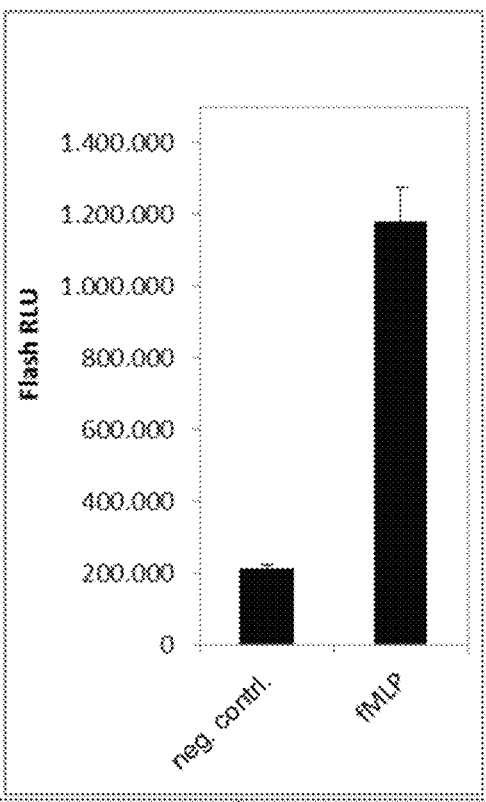
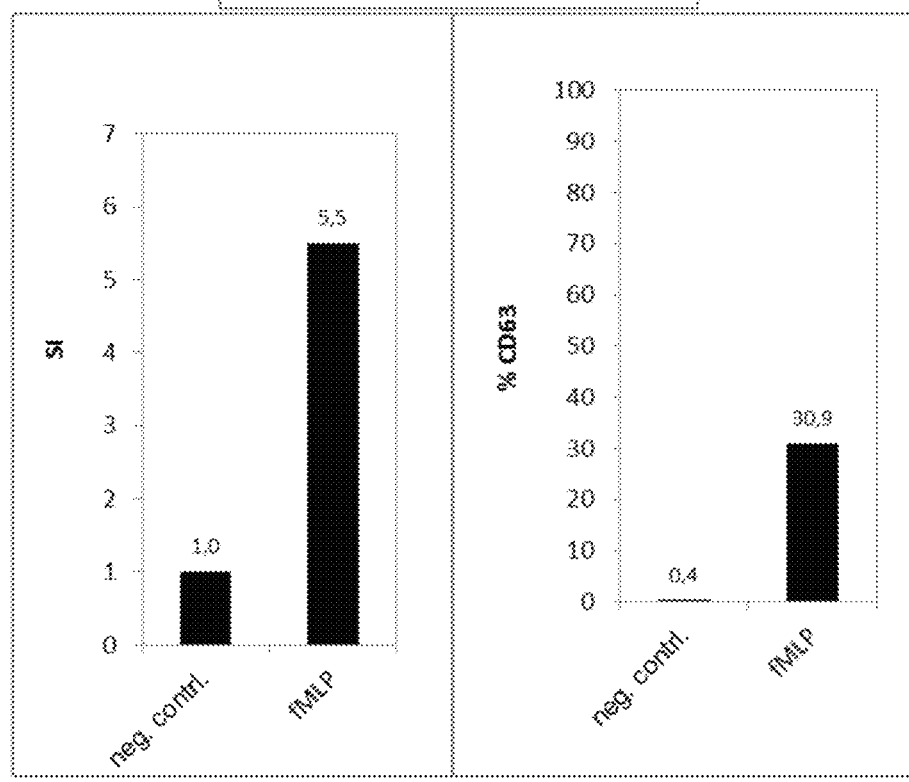
FIG. 12B          FIG. 12C

METHOD FOR DETECTING BASOPHIL ACTIVATION

The present invention relates to a method for diagnosing an allergy, comprising the steps of bringing basophils from a whole blood sample of a patient into contact with an allergen in an aqueous solution in the presence of the whole blood, with a volume content of whole blood in the aqueous solution of at least 20 percent by volume, under conditions that allow activation of the basophils by the allergen, enrichment of the basophils from step a) and detection of activated basophils, wherein the detection is carried out in that a marker characteristic of activated basophils is detected by means of chemiluminescence; and a kit comprising a vessel for bringing the basophils into contact with the allergen, wherein the vessel is preferably a microtiter plate, optionally an allergen, an agent for detecting a marker characteristic of activated basophils by means of chemiluminescence, wherein the agent is preferably a ligand against the marker provided with a label capable of chemiluminescence and the ligand more preferably is a monoclonal antibody, optionally an agent for stopping activation of the basophils, an optionally immobilizable ligand that binds to a polypeptide located on the cell surface of basophils independently of its activation state, wherein the ligand is preferably a monoclonal antibody against the polypeptide, and optionally an agent for lysing and/or removing erythrocytes.

In diagnosing allergies of the immediate type, also referred to as type I allergies, which are based on an IgE-mediated immune response, the primary method used is to take a thorough patient history and then carry out skin tests such as skin prick tests or challenge tests, which are the gold standard in allergy diagnosis. As a supplement, in vitro tests are used by means of which the presence of specific IgE antibodies against one or more than one specified allergen is detected.

In order to carry out such detection, allergens are bound to matrices such as sponges, membranes or beads and brought into contact with patient sera. After this, the amount of bound IgE is determined using a labeled anti-human IgE antibody.

The advantages of specific IgE determination in vitro lie in the fact that it is easy to carry out, standardizable, and scalable. In many cases, however, this method cannot distinguish between a clinically relevant allergy and simple sensitization.

Further drawbacks are the poor availability of many antigens and a possible conformational change in the allergen because of its coupling to a matrix, which can alter the affinity for the IgE antibody to be detected. In many cases, allergen extracts can be standardized only with difficulty or not at all. In addition, smaller allergens must be bound to carrier molecules such as serum albumin. Furthermore, the allergen specificity of IgE antibodies in serum and membrane-bound IgE antibody for effector cells such as basophils and mast cells are not necessarily the same, as only a slow exchange of dissolved and bound IgE takes place. Finally, other factors that cannot be reflected in an in vitro test for detecting specific IgE antibody determine whether a cellular allergic reaction is actually triggered, the overall ratio of total IgE to specific IgE in the blood or the affinity of the antibody.

Particularly in cases where IgE and skin tests yield unclear results, it is therefore advisable to use as a supplement a cellular test system such as the basophil degranulation test or the basophil activation test (BAT). Ordinarily, the term "BAT" is used with reference to flow cytometry tests.

The particular advantage of cellular tests over specific IgE antibody determination, which determines only the dissolved, biologically inactive IgE content in the serum, is that they detect the actual cellular biological reaction that is triggered by binding of the allergen to receptor-bound IgE antibody on the cell surface of the basophils and the cross-linking thereof. Cellular tests also make it possible to determine the threshold of degranulation capacity. They are needed in particular after immunotherapy in order to monitor therapeutic success in the patient.

As a rule, cellular tests are carried out by first bringing patient blood into contact with the allergen. If the patient has already been sensitized, this results in binding of the allergen to receptor-bound allergen-specific IgE antibodies located on the cell surface of the basophils. This leads to crosslinking of the IgE receptors, which in turn triggers degranulation of the basophilic granulocytes and thus the release of mediators from intracellular granules. These mediators, such as histamine, leukotrienes and tryptase, can be quantified in the supernatant by means of enzyme immunoassays. Secretion of the mediators goes hand in hand with an elevated cell surface concentration of markers such as CD63 or CD203c, which were previously located on the membranes of the intracellular granules and thus also indicate a cellular reaction. Secretion of the mediators thus indicates a cellular reaction to the allergen.

This elevated surface concentration has been detected to date in routine diagnosis by flow cytometry using antibodies against the activation-specific cell surface markers that are bound to a fluorophore. In this case, the cells to be investigated flow individually in a liquid stream through a thin measuring chamber and pass through a plurality of laser beams of different wavelengths, wherein a scattered light characteristic of each cell type is produced, and at the same time, depending on the respective wavelength, the fluorophores coupled to the antibodies are stimulated, provided that activated cells are present. The light emitted by the excited fluorophore and the scattered light are picked up by detectors.

Drawbacks of this test system are the high acquisition cost of a flow cytometer, the complexity of the test results, which can only be interpreted by trained technical personnel, and the difficulty of standardization. In all cases, moreover, it is only possible to measure one sample at a time with a single device.

A further problem according to the invention relates to the quality of samples containing activatable basophils. The quality of the samples and thus their suitability for diagnostic methods depends on whether they are obtained, transported, and stored according to professional standards. For example, the cells can die if they are exposed to heat or unsuitable buffers.

If the quality is insufficient, this may cause false negative results, which means that a negative result does not indicate that the patient is not allergic, but simply that the patient's sample is of insufficient quality, or more precisely, that it contains no or too few activatable basophils.

It is particularly inefficient if the deficient quality of a sample is detected only by carrying out a complicated method such as flow cytometry.

There is therefore a need for a method or methods suitable for determining the quality of a sample in an efficient manner, i.e. using a process suitable for high throughput. Although such a method is not carried out using an allergen and therefore does not provide a diagnostically useful result, it does allow a prediction to be made as to whether the sample quality is suitable for a diagnostic method carried out in a separate batch. This method can be carried out before, after, or in parallel with the diagnostic method. This method or the reagents used therein can serve to determine the number or content of activatable basophils in a cell preparation, preferably a sample.

DE 10235310 discloses a test in which the activation of basophils is detected using a fluorescent calcium dye. Blood fractionated by density gradient centrifugation is used.

WO 2012/044756, US 2009/0246805, WO 98/32014 and EP 2037269 disclose flow cytometric tests for detecting the activation of basophils.

Against this background, an object of the invention is to provide a method and reagents suitable for said method by means of which the above-mentioned drawbacks of the methods described in the prior art can be overcome, in particular a basophil activation test that can be carried out with a system other than a flow cytometer.

In particular, an object is to provide a system that allows the simultaneous processing of a plurality of samples in a high-throughput method. Furthermore, reproducibility and standardizability are to be ensured.

This and further objects are achieved by the subject matter of the present invention, in particular by the subject matter of the attached independent claims, wherein preferred embodiments are given in the dependent claims.

In a first aspect, the problem of the invention is solved by means of a method for diagnosing an allergy, preferably a method suitable for high throughput, comprising the following steps:
  a) bringing into contact of basophils from a whole blood sample of a patient with an allergen in an aqueous solution in the presence of whole blood, with a volume content of whole blood in the aqueous solution of at least 20 percent by volume, under conditions that allow activation of the basophils by the allergen,
  b) enrichment of the basophils from step a) and
  c) detection of activated basophils,
wherein the detection in step c) is carried out in that a marker characteristic of activated basophils is detected by means of chemiluminescence.

Alternatively, the problem is solved in a first aspect by means of a method for diagnosing an allergy, comprising the following steps:
  a) bringing into contact of basophils from a whole blood sample of a patient with an allergen in an aqueous solution in the presence of whole blood, with a volume content of whole blood in the aqueous solution of at least 20 percent by volume, under conditions that allow activation of the basophils by the allergen,
  b) enrichment of the basophils from step a) and
  c) detection of activated basophils,
    wherein the detection in step c) is carried out in that a marker located on the surface of basophils is detected by means of chemiluminescence,
    wherein in step b), basophils are enriched in that they bind to a ligand, which binds specifically to a polypeptide that is a marker characteristic of activated basophils,
    and/or the detection in step c) is carried out in that a marker characteristic of activated basophils is detected by means of chemiluminescence.

In a preferred embodiment, the whole blood is unprocessed whole blood.

In a further preferred embodiment, step a) is carried out in an aqueous solution with a whole blood content of at least 30, preferably 35, more preferably 40, more preferably 45 percent by volume.

In a further embodiment, the method comprises the step of stopping the activation of basophils, preferably before step b).

In a further embodiment, the basophils in step b) are enriched in that they bind to a ligand that binds specifically to a polypeptide located in basophils on the cell surface. This polypeptide can be a polypeptide located on the cell surface of the basophils independently of its activation state and/or a marker characteristic of activated basophils, preferably a further marker characteristic of activated basophils, which differs from the marker that is detected according to the invention by means of chemiluminescence. In a particularly preferred embodiment, it is a polypeptide that is located on the cell surface of basophils independently of their activation state.

In a further embodiment, the ligand that binds specifically to a polypeptide located on the cell surface of basophils independently of their activation state is a monoclonal antibody against the polypeptide.

In a preferred embodiment, the basophils are immobilized in step b).

In a preferred embodiment, the basophils are immobilized in step b) on a bead, preferably a magnetic bead.

In a preferred embodiment, the basophils are washed after immobilization.

In a preferred embodiment, the erythrocytes are lysed and removed in step b).

In a preferred embodiment, the erythrocytes are removed by centrifugation before immobilization of the basophils.

In a preferred embodiment, the detection in step c) is carried out using a ligand provided with a label capable of chemiluminescence against the marker located on the surface of basophils, preferably a marker that is characteristic of activated basophils.

In a preferred embodiment, the ligand provided with a label capable of chemiluminescence is a monoclonal antibody that itself comprises a label capable of chemiluminescence or binds to a secondary antibody with a label capable of chemiluminescence.

In a preferred embodiment, steps a), b) and c) are carried out in a microtiter plate.

In a preferred embodiment, step a) is carried out before steps b) and c).

In a further aspect, the object of the invention is achieved by means of a kit comprising a vessel for bringing the basophils into contact with the allergen, wherein the vessel is preferably a microtiter plate, optionally an allergen, an agent for detecting a marker characteristic of activated basophils by means of chemiluminescence, wherein said agent is preferably a ligand against the marker provided with a label capable of chemiluminescence and the ligand more preferably is a monoclonal antibody, optionally an agent for stopping activation of the basophils, an optionally immobilizable ligand that binds to a polypeptide located on the cell surface of basophils independently of its activation state, wherein the ligand is preferably a monoclonal antibody against the polypeptide, and optionally an agent for lysing and/or removing erythrocytes.

Alternatively, the problem is solved in a further aspect by means of a kit comprising a vessel for bringing the basophils into contact with the allergen, wherein the vessel is preferably a microtiter plate, optionally an allergen, a ligand against a polypeptide located on the cell surface of basophils for the enrichment of basophils, and a ligand against a marker for detection located on the cell surface of basophils, wherein the ligand against the marker for detection located on the surface of basophils comprises a label capable of chemiluminescence, wherein the label capable of chemiluminescence can be an enzyme that catalyzes a chemiluminescence reaction or a molecule that itself generates a chemiluminescence signal under suitable conditions, wherein the enzyme in the former case is contained in the kit in combination with a substrate solution capable of chemiluminescence, and wherein the polypeptide located on the cell surface of basophils and/or the marker located on the cell surface of basophils is characteristic of activated basophils. Optionally, the kit comprises an agent for stopping activation of the basophils. Optionally, the kit comprises an agent for lysing and/or removing erythrocytes.

The reagents contained in a kit according to the invention can also be used with or without a vessel for bringing the basophils into contact with the allergen to provide a kit for diagnosing an allergy.

In a further aspect, the problem is solved by use of a ligand against a polypeptide located on the cell surface of basophils for the enrichment of basophils together with a ligand against a marker for detection located on the cell surface of basophils in order to diagnose an allergy, for producing a kit for diagnosing an allergy, or for screening candidate active ingredients for the treatment of an allergy to an allergen, wherein the ligand against the marker for detection located on the surface of basophils comprises a label capable of chemiluminescence, wherein the label capable of chemiluminescence can be an enzyme that catalyzes a chemiluminescence reaction or a molecule that itself generates a chemiluminescence signal under suitable conditions, wherein the enzyme in the former case is used in combination with a substrate solution capable of chemiluminescence, and wherein the polypeptide located on the cell surface of basophils and/or the marker located on the cell surface of basophils is characteristic of activated basophils.

In a further aspect, the problem is solved by use of a ligand against a ligand characteristic of activated basophils for diagnosing an allergy, for producing a kit for diagnosing an allergy, or for screening candidate active ingredients for the treatment of an allergy to an allergen, wherein the ligand has a label capable of chemiluminescence.

In a preferred embodiment, the use is for increasing sensitivity, preferably in a high-throughput method.

The present invention relates to a method for diagnosing an allergy first comprising the step a) of bringing into contact of basophils from a whole blood sample of a patient with an allergen in an aqueous solution. The whole blood sample is preferably whole blood with substances having an anticoagulant action. The whole blood is added to the aqueous solution before the basophils are actually brought into contact with the allergen in an amount such that its final volume content in the aqueous solution is at least 20, more preferably 25, 30, 35, 40, 45, 50, 55, 60, 65, 70, 75 or 80 percent by volume. The presence of the whole blood causes bringing of the basophils into contact with the allergen to take place under virtually physiological conditions.

The method is preferably a method suitable for high throughput. This is understood in a preferred embodiment to refer to a method that allows parallel processing of a plurality of samples, for example at least 2, 4, 8, 16 or 32 samples, wherein the method steps, which take up at least 50, more preferably 60, 70, 80 or 90% of the processing time required for an individual sample, can essentially take place simultaneously with processing of the samples. This includes methods in which the actual measuring process is carried out using a measuring device for all of the samples successively, but the individual, non-parallel processing time for a sample does not exceed 5, more preferably 4, 3, 2, 1 min or 30 sec. For example, methods suitable for high throughput comprise chemiluminescence measurement in microtiter plates suitable for this purpose. In contrast, for example, flow cytometry is not a method suitable for high throughput.

The whole blood is preferably unprocessed whole blood. In a preferred embodiment, the term "unprocessed whole blood" as used herein is understood to mean that although the blood can be diluted or chemical substances can be added to it for preservation, preferably substances having an anticoagulant action such as heparin, it is not fractionated, for example by means of a centrifugation method such as density gradient centrifugation.

Step a) can also be carried out with more than one allergen and/or an allergen in more than one concentration in different, parallel-processed batches. In particular, the antigen can be used in two or more, preferably three or more different concentrations in a corresponding number of parallel batches. Preferably, a positive control and a negative control are additionally carried out. In a preferred embodiment, the allergen is a material selected from the group comprising mite cultures and mite feces of the taxonomic kingdom Animalia, phylum Arthropoda; scales, hair, saliva, feces or other secretions originating from the taxonomic kingdom Animalia, phylum Chordata; spores or particles originating from the taxonomic kingdom Fungi, phylum Ascomycota; pollen originating from the taxonomic class Coniferopsida, pollen originating from the taxonomic kingdom Plantae, class Magnoliopsida, pollen originating from the taxonomic kingdom Plantae, class Liliopsida; poison or secretions originating from the taxonomic kingdom Animalia, phylum Arthropoda; or rubber or products comprising a rubber originating from trees of the taxonomic kingdom Plantae, class Magnoliopsida.

In a preferred embodiment, the allergen is a drug selected from the group comprising antibiotics, more preferably β-lactams, more preferably from the group comprising penicillin G, penicillin V, PPL, MDM, amoxicillin and ampicillin; cephalosporins, more preferably from the group comprising cefazolin, cefamandole, cefaclor, cefonaxime, ceftazidime, cefotaxime, ceftazidime, cefepime; carbapenems, monobactams, β-lactamase inhibitors, more preferably clavulanic acid; macrolides, aminoglycosides, rifamycins, glycopeptides, polypeptides, tetracyclines, imidazoles, quinolones, pyrazolones, more preferably sulfamethoxazole; streptogramins, nitrofurans, isoniazids, pentamidines; antiseptics, more preferably chlorhexidine, fungicides, antiviral agents, antimalarials, analgesics, COX-2 inhibitors and non-steroidal anti-inflammatories, preferably from the group comprising aspirin, lys-aspirin, Ibuprofen, ketoprofen, diclofenac, naproxen, paracetamol, dipyrone, indomethacin, mefenamic acid, phenylbutazone and propyphenazone; neuromuscular blockers, preferably from the group comprising suxamethonium, atracurium, cis-atracurium, mivacurium, pancuronium, rocuronium, vecuronium and succinylcholine; hypnotics and local anesthetics, preferably from the group comprising midazolam, propofol, thiopental, fentanyl and lidocaine; tranquilizers; opioids; radiocontrast agents, preferably from the group comprising ionic iodinated contrast agents, nonionic iodinated contrast agents, isosulfan blue, patent blue and methylene blue; proton pump inhibitors, anticonvulsants and neuroleptics, preferably from the group comprising carbamazepine, phenytoin and valproic acid; antipsychotics; antidepressants; dopamine; antihistamines; corticosteroids and glucocorticoids; chemotherapeutic agents and immunosuppressants; diuretics; anticoagulants; vasoconstrictors and vasodilators; cardiac drugs, preferably from the group comprising statins, ACE inhibitors, alpha receptor blockers, beta receptor blockers, calcium antagonists and antihypertensives; (anti)tumor drugs; (anti) thyroid drugs; estrogens; heparins and derivatives; insulins; streptokinases and urokinases.

In a preferred embodiment, the allergen is a colloid expander, plasma expander or auxiliary, preferably selected from the group comprising albumin, dextran, gelatins, hetastarch, pentastarch, sinistrin, polidocanol 600 (Aethoxysklerol), lactose, carboxymethylcellulose, hydroxypropylcellulose, protamine and aprotinin.

In a preferred embodiment, the allergen is a food additive, preferably selected from the group comprising food preservatives, food dyes, food finishing agents, antioxidants and emulsifiers.

In a preferred embodiment, the allergen is an environmental pollutant or harmful substance, preferably selected from the group comprising isocyanates, isothiazolinones, formaldehyde, ethylene oxide, phthalic anhydride, chloramine-T, DMSO, latex and enzymes used in the baking agent, food processing, and washing industry.

In a preferred embodiment, the allergen is a material selected from the group comprising a mite culture and/or feces selected from the group composed of mites of a genus selected from *Acarus, Glycyphagus, Lepidoglyphus, Tryophagus, Blomia, Dermatophagoides, Euroglyphus, Blatella* and *Periplaneta*; scales, hair, saliva or feces of an animal of a genus selected from *Canis, Felis* or *Equus*; yeast, mold, or fungi of a genus selected from the group composed of *Cladosporium, Aspergillus, Penicillium, Alternaria* and *Candida*; pollen of a genus selected from the group composed of *Chamaecyparis, Cryptomeria, Cupressus, Juniperus, Anthoxanthum, Cynodon, Dactylis, Festuca, Holcus, Hordeum, Lolium, Oryza, Paspalum, Phalaris, Phleum, Poa, Secale, Sorghum, Triticum, Zea, Ambrosia, Artemisia, Alnus, Betula, Corylus, Fraxinus, Olea* and *Platanus*; venom from an insect of a genus selected from the group composed of *Apis Bombus, Dolichovespula, Polistes, Polybia, Vespa* and *Vespula*; and rubber or products comprising a rubber originating from the genus Hevea.

In a preferred embodiment, the allergen is a material selected from the group comprising shrimps or a shrimp-containing food of the taxonomic kingdom Animalia, phylum Arthropoda; lobsters or a lobster-containing food of the taxonomic kingdom Animalia, phylum Arthropoda; fruits, legumes, cereal, or beans originating from taxonomic kingdom Plantae, class Liliopsida or a food product comprising such fruits, legumes, cereal, and/or beans; fruits, legumes, cereal, or beans originating from the taxonomic kingdom Plantae, class Magnoliopsida a food product comprising such fruits, legumes, cereal, and/or beans; and a nut or a nut-containing food of the taxonomic kingdom Plantae, class Magnoliopsida.

In a preferred embodiment, the allergen is material selected from the group comprising cow's milk, cow's-milk-containing food, chicken protein, chicken-containing food, fish or fish-containing food.

In a preferred embodiment, the allergen is material selected from the group comprising *Hordeum, Oryza, Secale, Triticum, Zea, Arachis, Corylis, Juglans, Prunus, Anacardium, Pistacia* and *Glycine*.

In a preferred embodiment, the allergen is a polypeptide comprising an antigen or a variant thereof from the group comprising Aca s 13, Gly d 2, Lep d 2, Lep d 5, Lep d 7, Lep d 10, Lep d 13, Tyr p 2, Tyr p 3, Tyr p 10, Tyr p 13, Tyr p 24, Blot 1, Blot 2, Blot 3, Blot 4, Blot 5, Blo t 6, Blot 10, Blo t 11, Blo t 12, Blo t 13, Blo t 19, Blo t 21, Der f 1, Der f 2, Der f 3, Der f 6, Der f 7, Der f 10, Der f 11, Der f 13, Der f 14, Der f 15, Der f 16, Der f 17, Der f 18, Der f 22, Der m 1, Der p 1, Der p 2, Der p 3, Der p 4, Der p 5, Der p 6, Der p 7, Der p 8, Der p 9, Der p 10, Der p 11, Der p 14, Der p 20, Der p 21, Der p 23, Eur m 1, Eur m 2, Eur m 3, Eur m 4, Eur m 14, Bla g 1, Bla g 2, Bla g 4, Bla g 5, Bla g 6, Bla g 7, Bla g 8, Per a 1, Per a 3, Per a 6, Per a 7, Per a 9, Per a 10, Can f 1, Can f 2, Can f 3, Can f 4, Can f 5, Can f 6, Fel d 1, Fel d 2, Fel d 3, Fel d 4, Fel d 5w, Fel d 6w, Fel d 7, Fel d 8, Equ c 1, Equ c 2, Equ c 3, Equ c 4 and Equ c 5, Cla c 9m, Cla c 14, Cla h 2, Cla h 5, Cla h 6, Cla h 7, Cla h 8, Cla h 9, Cla h 10, Cla h 12, Asp fl 13, Asp f 1, Asp f 2, Asp f 3, Asp f 4, Asp f 5, Asp f 6, Asp f 7, Asp f 8, Asp f 9, Asp f 10, Asp f 11, Asp f 12, Asp f 13, Asp f 15, Asp f 16, Asp f 17, Asp f 18, Asp f 22, Asp f 23, Asp f 27, A5p f 28, A5p f 29, Asp f 34, Asp n 14, Asp n 18, Asp n 25, Asp o 13, Asp o 21, Pen b 13, Pen b 26, Pen ch 13, Pen ch 18, Pen ch 20, Pen ch 31, Pen ch 33, Pen ch 35, Pen c 3, Pen c 13, Pen c 19, Pen c 22, Pen c 24, Pen C 30, Pen c 32, Pen o 18, Fus c 1, Fus c 2, Alt a 1, Alt a 3, Alt a 4, Alt a 5, Alt a 6, Alt a 7, Alt a 8, Alt a 10, Alt a 12, Alt a 13, Cand a 1, Cand a 3 and Cand b 2, Cha o 1, Cha o 2, Cup a 1, Cups 1, Cups 3, Jun a 1, Jun a 2, Jun a 3, Juno 4, Jun s 1, Jun v 1 and Jun v 3, Ant o 1, Cyn d 1, Cyn d 7, Cyn d 12, Cyn d 15, Cyn d 22w, Cyn d 23, Cyn d 24, Dac g 1, Dac g 2, Dac g 3, Dac g 4, Dac g 5, Fes p 4, Hol I 1, Hol I 5, Hor v 1, Hor v 5, Lol p 1, Lol p 2, Lol p 3, Lol p 4, Lol p 5, Lol p 11, Pas n 1, Pha a 1, Pha a 5, Phl p 1, Phl p 2, Phl p 4, Phl p 5, Phl p 6, Phl p 7, Phl p 11, Phl p 12, Phl p 13, Poa p 1, Poa p 5, Sec c 1, Sec C 5, Sec c 20, Sor h 1, Tri a 15, Tri a 21, Tri a 27, Tri a 28, Tri a 29, Tri a 30, Tri a 31, Tri a 32, Tri a 33, Tri a 34, Tri a 35, Zea m 1, Zea m 12, Amb a 1, Amb a 2, Amb a 3, Amb a 4, Amb a 5, Amb a 6, Amb a 7, Amb a 8, Amb a 9 and Amb a 10, Amb p 5, Amb t 5, Art v 1, Art v 2, Art v 3, Art v 4, Art v 5, Art v 6, Aln g 1, Aln g 4, Bet v 1, Bet v 2, Bet v 3, Bet v 4, Bet v 6, Bet v 7, Cora 10, Fra e 1, Ole e 1, Ole e 2, Ole e 3, Ole e 4, Ole e 5, Ole e 6, Ole e 7, Ole e 8, Ole e 9, Ole e 10, Ole e 11, Pla a 1, Pla a 2, Pla a 3, Pla or 1, Pla or 2 and Pla or 3, Api c 1, Api d 1, Api m 1, Api m 2, Api m 3, Api m 4, Api m 5, Api m 6, Api m 7, Api m 8, Api m 9, Api m 10, Api m 11, Born p 1, Born p 4, Born t 1, Born t 4, Dol a 5, Dol m 1, Dol m 2, Dol m 5, Pol a 1, Pol a 2 and Pol a 5, Pol d 1, Pol d 4, Pol d 5, Pole 1, Pole 4 and Pole 5, Pol f 5, Pol g 1, Pol g 5, Polyp 1, Poly s 5, Vesp c 1, Vesp c 5, Vesp ma 2, Vesp ma 5, Vesp m 1, Vesp m 5, Ves g 5, Ves m 1, Ves m 2, Ves m 5, Ves p 5, Ves s 1, Ves s 5, Ves vi 5, Ves v 1, Ves v 2, Ves v 3, Ves v 5, Hev b 1, Hev b 2, Hev b 3, Hev b 4, Hev b, 5 Hev b 6, Hev b 7, Hev b 8, Hev b 9, Hev b 10, Hev b 11, Hev b 12, Hev b 13 and Hev b 14, Hor v 12, Hor v 15, Hor v 16, Hor v 17, Hor v 21, Ory s 12, Sec c 20, Tri a 12, Tri a 14, Tn a 18, Tri a 19, Tri a 21, Tri a 25, Tri a 26, Tri a 36, Zea m 14, Zea m 25, Ara h 1, Ara h 2, Ara h 3, Ara h 4, Ara h 5, Ara h 6, Ara h 7, Ara h 8, Ara h 9, Ara h 10, Ara h 11, Cor a 1, Cor a 2, Cor a 8, Cor a 9, Cor a 11, Cor a 12, Cor a 13, Cor a 14, Jug n 1, Jug n 2, Jug r 1, Jug r 2, Jug r 3, Jug r 4, Pru du 3, Pru du 4, Pru du 5, Pru du 6, Ana o 1, Ana o 2, Ana o 3, Pis v 1, Pis v 2, Pis v 3, Pis v 4, Pis v 5, Gly m 1, Gly m 2, Gly m 3, Gly m 4, Gly m 5 and Gly m 6.

Step a) can be carried out in a vessel for bringing the basophils into contact with the allergen. In a preferred embodiment, the vessel is a microtiter plate. In a further preferred embodiment, the allergen or allergens is/are first placed in the vessel in freeze-dried form and are converted to the liquid phase on addition of aqueous solution and the whole blood sample.

In a preferred embodiment, the antigen is Ara h 7 isotype 7.0201 (EP 17000245). In a further preferred embodiment, the antigen is the macadamia nut antigen described in EP 16000165.7. Modified polypeptides can also be used as antigens, for example the oleosin constructs disclosed in EP 15001277.1.

In a preferred embodiment, the method comprises the step of stopping the activation of the basophils, preferably before step b). The person skilled in the art is familiar with various means of stopping the activation reaction, for example addition of calcium-binding agents such as EDTA, addition of an azide, preferably sodium azide, or cooling the sample, preferably to a temperature of at most 4° C.

Preferably, after step a), the basophils are enriched in step b). In a preferred embodiment, the term "enrich" as used herein is understood to mean that the number of the basophils relative to the total number of all cells or the number of leukocytes, preferably to the number of leukocytes in the whole blood sample is increased, preferably by a factor of at least 2, 5, 10, 20, 50, 100 or 1000, more preferably at least 1000. This preferably takes place in that they bind a ligand that specifically binds via a first binding site to a polypeptide that is expressed in basophils depending on or independently of, preferably independently of, their activation state and is located on their cell surface, while in other cells, or at least in the majority of other cells, it is present there only to a minor extent or preferably not at all. This polypeptide must thus be suitable as a selecting agent for enriching the basophils relative to the total number of cells in a blood sample. In this case, it is acceptable if the enrichment is not completely successful, but a small number of the other cells remain in the sample, for example dendritic cells. Preferably, the polypeptide is selected from the group of polypeptides located on the cell surface of the basophils independently of their activation state, which comprises CD123 (database code NM_002183), CD193 (NP_001828), FcεRI (NM_002001), IgE, CD203c (NM_005021) and CRTH2 (NM_004778), and is preferably CD123 or IgE, more preferably CD123. All of the database codes used in this application refer to the sequence that was available online on the filing date of the earliest application giving rise to priority in the database specified by the number. The ligand is preferably a monoclonal antibody against the polypeptide, preferably a monoclonal antibody against CD123 or IgE, more preferably against CD123 (Agis, H., Füreder, W., Bankl, H. C., Kundi, M., Sperr, W. R., Wllheim, M., . . . & Valent, P. (1996). Comparative immunophenotypic analysis of human mast cells, blood basophils and monocytes. *Immunology*, 87(4), 535-543; Sainte-Laudy, J. Sabba, A., Vallon C, Guerin J C (1998). Analysis of anti-IgE and allergen induced human basophil activation by flow cytometry. Comparison with histamine release. *Inflamm Res*. 47(10), 401-8.). In an even more preferable embodiment, an isolated monoclonal antibody is used. In a further preferred embodiment, the basophils bind to more than one ligand, which specifically binds via a first binding site to a polypeptide that is expressed in basophils depending on or independently of their activation state and is located on their cell surface, wherein the polypeptide is preferably selected from the group of peptides expressed on the cell surface of the basophils independently of their activation state, which comprises CD123 (database code NM_002183), CD193 (NP_001828), FcεRI (NM_002001), IgE, CD203c (NM_005021) and CRTH2 (NM_004778), more preferably two or three ligands, wherein even more preferably one of the ligands is CD123. A polypeptide that is expressed in basophils depending on their activation state and is located on their cell surface is preferably selected from the group comprising basogranulin (Mochizuki A, McEuen A R, Buckley M G, Walls A F. The release of basogranulin in response to IgE-dependent and IgE-independent stimuli: validity of basogranulin measurement as an indicator of basophil activation. *J. Allergy Clin. Immunol*. 2003 July; 112(1): 102-8), 2D7 antigen (CL Kepley, SS Craig and LB Schwartz. Identification and partial characterization of a unique marker for human basophils. *J Immunol* Jun. 15, 1995, 154 (12) 6548-6555), avidin binding mediator (Joulia R, Valitutti S, Didier A, Espinosa E. Direct monitoring of basophil degranulation by using avidin-based probes. *J Allergy Clin Immunol*. 2017), CD13 (NM_001150), CD45 (NM_001150), CD63 (NP_001244318.1), CD107a (NM_00556), CD11b (NM_000632), CD62L (NM_000655), CD11c (XM_011545852), CD164 (NM_001142401), CD45 (NM_001267798) and CD203c (NM_005021), and is preferably CD63 (Knol, E. F., Mul, F. P., Jansen, H., Calafat, J., & Roos, D. (1991). Monitoring human basophil activation via CD63 monoclonal antibody 435. *Journal of Allergy and Clinical Immunology*, 88(3), 328-338.).

Preferably, the ligand comprises a second binding site that can be used to immobilize it on a solid carrier, preferably specifically, when the carrier shows complementary binding capacity, more specifically, the capacity to bind specifically to the ligands. Preferably, the ligand comprises a molecule that itself has a binding capacity selected from the group comprising biotin, streptavidin, His tag, GST, avidin, neutravidin, protein A, protein G, protein L, S tag and MBP. The solid carrier is preferably a carrier from the group comprising a bead, preferably a magnetic bead, a microtiter plate, a reaction vessel composed of plastic and a reaction vessel composed of glass. In a particularly preferred embodiment, the carrier is a bead, preferably a magnetic bead, and the aqueous solution comprising the bead is located in a well of a microtiter plate. In a preferred embodiment, the aqueous solution is continuously mixed in step a) and/or step b), for example by stirring or agitation.

In a preferred embodiment of the method, the lysing and subsequent removal of erythrocytes are preferably carried out in step b). Methods for lysing erythrocytes are known to the person skilled in the art, for example as described in U.S. Pat. Nos. 4,902,613, 6,143,567 or WO 85/05640. For example, hypotonic lysis can be carried out with water alone or in the presence of diethylene glycol, formaldehyde and citric acid (U.S. Pat. No. 4,902,613).

Removal of the erythrocytes is preferably carried out by centrifugation.

The activation of basophils is detected according to the invention in that the surface concentration of a marker characteristic of activation is detected by means of chemiluminescence. Preferably, the marker is selected from the group comprising basogranulin (Mochizuki A, McEuen A R, Buckley M G, Walls A F. The release of basogranulin in response to IgE-dependent and IgE-independent stimuli: validity of basogranulin measurement as an indicator of basophil activation. *J. Allergy Clin. Immunol*. 2003 July; 112(1): 102-8), 2D7 antigen (CL Kepley, SS Craig and LB Schwartz. Identification and partial characterization of a unique marker for human basophils. *J Immunol* Jun. 15, 1995, 154 (12): 6548-6555), avidin-binding mediator (Joulia R, Valitutti S, Didier A, Espinosa E. Direct monitoring of basophil degranulation by using avidin-based probes. *J Allergy Clin Immunol*. 2017), CD13 (NM_001150), CD45 (NM_001150), CD63 (NP_001244318.1), CD107a (NM_00556), CD11 b (NM_000632), CD62L (NM_000655), CD11c (XM_011545852), CD164 (NM_001142401), CD45 (NM_001267798) and CD203c (NM_005021), and is preferably CD63 (Knol, E. F., Mul, F. P., Jansen, H., Calafat, J., & Roos, D. (1991). Monitoring human basophil activation via CD63 monoclonal antibody 435. *Journal of Allergy and Clinical Immunology*, 88(3), 328-338). It is possible to detect more than one of these markers. For this purpose, a ligand against a marker characteristic of activated basophils, preferably a monoclonal antibody, is preferably provided with a label capable of chemiluminescence. In an even more preferable embodiment, an isolated monoclonal antibody is used.

The label capable of chemiluminescence can be an enzyme that catalyzes a chemiluminescence reaction or a molecule that itself generates a chemiluminescence signal under suitable conditions, preferably the latter molecule, more preferably an acridinium ester or acridinium sulfonamide. In a step carried out before step a), a ligand against a marker that is characteristic of activated basophils can be coupled to a label capable of chemiluminescence. For example, the monoclonal antibody can be mixed with an acridinium ester (AE). AE compounds are high specific activity labels that are already used in automated assays for clinical diagnosis (I Weeks, I Beheshti, F McCapra, A K Campbell, J S Woodhead. Acridinium esters as high specific activity labels in immunoassay. *Clin Chem* 29: 1474-1479 (1983)). Coupling of AE compounds to antibodies is well-established and is usually achieved via functional groups such as N-hydroxysuccinimidyl (NHS) in the phenol ring. For this purpose, the purified antibody is reacted at room temperature for a specified period of time with AE (e.g. NSP-SA-NHS, NSP-DMAE or NSP-DMAE-NHS from the firm Heliosense). After this, the labeled antibody is separated from the unreacted free AE using columns or other purification methods such as HPLC.

In a preferred embodiment, the acridinium ester has the following formula:

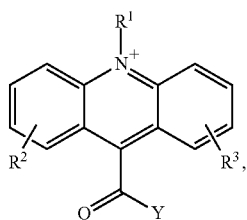

where R1 is an alkyl, substituted alkyl, aryl, or substituted aryl group and R2 and R3, independently of each other, are selected from the group comprising hydrogen or an alkyl, substituted alkyl, halogen, cyanide, hydroxy, alkoxy, thiol, or alkylmercapto group, Y is a leaving group, preferably with a pKa <12, preferably from the group comprising an aryloxy, substituted aryloxy, substituted alkoxy, mercapto, substituted mercapto, sulfonamidyl, substituted sulfonamidyl, N-hydroxylamine, or substituted N-hydroxylamine group, and the acridinium ester contains a group via which it can be or is coupled to a polypeptide, preferably an antibody, preferably an N-hydroxysuccinimidyl (NHS) group. Suitable compounds and methods are described in WO 2012/028167.

A chemiluminescence detection kit (e.g. from the firm Invitron) can also be used for detection. After washing of the unbound antibodies, the two triggers in succession (100 μl each; Trigger 1: contains hydrogen peroxide; Trigger 2: contains sodium hydroxide) are automatically added in the luminometer. In this case, the acridinium ester compound is oxidized under alkaline conditions, which produces light-emitting acridone. The signal is emitted in the form of a light flash (flash luminescence) that typically lasts 1-5 sec. The brief duration of emission requires that initiation and measurement be carried out directly in the detector. Suitable luminometers allow automatic trigger addition and detection of the signal in the microtiter plate. In order to achieve higher intensity, the entire signal is ordinarily integrated over the measurement interval.

An alternative is coupling of the antibody to an enzyme, preferably selected from the group comprising peroxidase, alkaline phosphatase and β-galactosidase, which can react with a substrate capable of chemiluminescence (Kricka L J. (2003). *Clinical applications of chemiluminescence. Analytica chimica acta*, 500(1): 279-286). In this case, depending on the enzyme, a substrate from the group of cyclic diacyl hydrazides, preferably luminol or isoluminol, acridine, dioxetane and derivatives thereof is used. The enzyme most commonly used for this purpose is horseradish peroxidase (HRP), which catalyzes the oxidation of luminol in the presence of hydrogen peroxide. The light thus emitted can be detected at a wavelength of 425 nm. A possible approach is described in Neupert, W., Oelkers, R., Brune, K., Geisslinger, G. A new reliable chemiluminescence immunoassay (CLIA) for prostaglandin E2 using enhanced luminol as substrate. Prostaglandins. 1996 November; 52(5): 385-401.

A further alternative is the use of electrogenerated chemiluminescence. Tris(2,2-bipyridyl)ruthenium(II) is already in use in several immunoassays (Xiaoming Zhou, Debin Zhu, Yuhui Liao, Weipeng Liu, Hongxing Liu, Zhaokui Ma & Da Xing (2014). Synthesis, labeling and bioanalytical applications of a tris(2,2-bipyridyl)ruthenium(II)-based electrochemiluminescence probe. *Nature Protocols*, Volume 9, pp. 1146-1159). After current is applied, chemiluminescence with an emission maximum of 620 nm is generated from the surrounding medium in the reaction of the ruthenium complex with tripropylamine (TPA). Preferably, the label capable of chemiluminescence is a metal complex capable of chemiluminescence, preferably comprising ruthenium.

In a preferred embodiment, the label capable of chemiluminescence catalyzes emission by another group or itself emits luminescence with a wavelength of 400 nm or more, preferably 400 nm to 650 nm, more preferably 400 nm to 550 nm, more preferably 405 nm to 500 nm, more preferably 405 nm to 490 nm, more preferably 410 to 490 nm, more preferably 410 to 450 nm, and most preferably 415 to 445 nm. Suitable compounds and methods are described in Natrajan et al. (2010) Enhanced immunoassay sensitivity using chemiluminescent acridinium esters with increased light output, Analytical Biochemistry, 27 Jul. 2010.

Preferably, a plurality of reactions is carried out in parallel in different wells of a microtiter plate and the chemiluminescence signals are detected using a commercially available plate luminometer (e.g. from Berthold Technologies). Here, the extent of basophil activation correlates with the intensity of or increase in the chemiluminescence signal relative to an unstimulated control. For a positive assessment, a threshold value depending on the test substance, which a person skilled in the art can determine on a routine basis, must be exceeded.

Preferably, the method is carried out in the order of step a) first, followed by step b), and finally step c). However, it is also possible to carry out step b) first, followed by step a)

and then step c). Alternatively, step b) and step c) can be carried out simultaneously or in an overlapping manner.

In a particularly preferred embodiment, after step a), both a ligand that binds specifically to a polypeptide located on the cell surface of basophils independently of their activation state and a ligand against the marker characteristic of activated basophils that is provided with a label capable of chemiluminescence are added to the aqueous solution with the basophils. More preferably, this is carried out in the presence of a carrier, wherein the ligand that binds specifically to a polypeptide located on the cell surface of basophils independently of their activation state is more preferably already immobilized or subjected to immobilization on a solid carrier such as a bead. After this, the aqueous solution can be changed and the immobilized basophils can be washed, wherein excess ligands and unbound cells are removed. What remain, if they are present, are basophils that are immobilized on the carrier via the ligand that binds specifically to a polypeptide located in basophils on the cell surface independently of their activation state. Among these immobilized basophils, those actually activated by contact with the allergen are characterized in that the ligand against the marker characteristic of activated basophils is bound to them. If the latter ligand is not itself provided with a label capable of chemiluminescence, one can if necessary, optionally after a washing step for removing excess ligands, add in a following step a secondary antibody with a label capable of chemiluminescence that binds to the latter ligand, wherein this antibody remains bound only to the activated basophils, and not to the unactivated basophils. Excess secondary antibody can be removed in a further washing step.

After this, chemiluminescence is measured. By means of this method, in particular in combination with the removal of erythrocytes, a level of sensitivity in detection of activation can be achieved that is comparable to that of the method using flow cytometry, despite the low content of basophils.

The method according to the invention and/or the kit according to the invention, or one or more than one reagent such as can be contained in the kit according to the invention, can also be used for screening candidate active ingredients in order to identify therapeutically effective active ingredients from a selection of candidate active ingredients. In this case, step a) is carried out after bringing the basophils into contact with a candidate active ingredient. In the case of a therapeutically effective candidate active ingredient, a lower level of activation is seen relative to a batch not containing a candidate active ingredient or containing an ineffective candidate active ingredient.

In a preferred embodiment, the term "candidate active ingredient" as used herein is understood to refer to a compound that is assumed to have a therapeutic effect in a patient or is to be investigated to determine whether it has such a therapeutic effect, preferably in the sense that it alleviates or prevents an allergic reaction. In a preferred embodiment, one or more than one already known active ingredient, which optionally is/are effective only in a subgroup of patients suffering from the allergy, is/are investigated to determine whether it/they is/are effective in a particular patient.

The invention relates to the use of the ligand comprising a label capable of chemiluminescence against a ligand characteristic of activated basophils for diagnosing an allergy or for producing a kit for diagnosing an allergy. The kit according to the invention can also be used for diagnosing an allergy. Production can comprise the coupling of a label capable of chemiluminescence to the ligand. The ligand can be used in a kit, a composition, or another combination with the ligand that binds specifically to a polypeptide located on the cell surface of basophils independently of their activation state.

A kit according to the invention can contain a reagent that activates basophils independently of the presence of an allergen. Such reagents are described in the prior art and comprise, but are not limited to, formyl-methionyl-leucyl-phenylalanine (fM LP), ionomycin, 12-myristate-13-acetate (PMA), fMLP and A23187, anti-human IgG, an anti-IgE receptor antibody C40/80 and sinomenines. The reagent is preferably fMLP and/or anti-Fc Epsilon-RI, more preferably fMLP.

The present invention further relates to a method and reagents suitable for this method used for determining the quality of a sample efficiently, i.e. by a method suitable for high throughput. Although such a method is not carried out using an allergen and therefore does not provide a diagnostically useful result, it does allow a prediction to be made as to whether the sample quality is suitable for a diagnostic method carried out in a separate batch.

The method according to the invention is carried out for this purpose, wherein the allergen is replaced by a reagent known to activate activatable basophils independently of the presence of an allergen.

As an additional or alternative positive control, one can add instead of the patient sample a basophil preparation in combination with an allergen or a reagent that is known to activate activatable basophils independently of the presence of an allergen, wherein the basophil preparation is known to be sufficiently reactive, i.e. is activatable by allergens. It can be used in a kit according to the invention alone or in combination with an allergen or a reagent that is known to activate activatable basophils independently of the presence of an allergen.

This method can be carried out before, after, or in parallel with the diagnostic method, or independently thereof.

The invention further relates to a non-diagnostic method for validating or verifying the reliability of a method for detecting basophil activation or determining the quality of the sample that contains basophils, preferably the activatability of basophils contained in the sample, comprising the following steps:
 a) bringing into contact of basophils from a whole blood sample of a patient with a reagent that activates the basophils independently of the presence of an allergen under conditions that allow activation of the basophils by the allergen,
 b) enrichment of the basophils from step a) and
 c) detection of activated basophils,
wherein the detection in step c) is carried out in that a marker characteristic of activated basophils is detected by means of chemiluminescence.

The reagent that activates basophils independently of the presence of an allergen can be formylmethionyl-leucyl-phenylalanine (fMLP; e.g. from Sigma, St Louis, Mo.) and/or an anti-IgE receptor antibody.

In a further aspect the invention relates to a method for treating an allergy, comprising:
(1) detecting activated basophils as described in the method for detecting activated basophils of the invention, and
(2) if activated basophils are detected, administering to the patient an effective amount of a therapeutic agent or treatment for type I hypersensitivity.

Type I hypersensitivity (or immediate hypersensitivity) is an allergic reaction provoked by reexposure to a specific type of antigen referred to as an allergen. Type I is not to be confused with type II, type III, or type IV hypersensitivities. In type 1 hypersensitivity, B-cells are stimulated (by CD4+ TH2 cells) to produce IgE antibodies specific to an antigen. The difference between a normal infectious immune response and a type 1 hypersensitivity response is that in type 1 hypersensitivity, the antibody is IgE instead of IgA, IgG, or IgM. During sensitization, the IgE antibodies bind to FcεRI receptors on the surface of tissue mast cells and blood basophils (Actor, J K (2012) Elsevier's Integrated Review Immunology and Microbiology (Second Edition), Chapter 7, pages 53-59). Type 1 hypersensitivity can be further classified into immediate and late-phase reactions. The immediate hypersensitivity reaction occurs minutes after exposure and includes release of vasoactive amines and lipid mediators, whereas the late-phase reaction ocurs 2-4 hours after exposure and includes the release of cytokines (Shiv Pillai M D; Abul K. Abbas MBBS; Andrew Wilson (2011). *Cellular and Molecular Immunology: with STUDENT CONSULT Online Access*. Philadelphia: Saunders. ISBN 1-4377-1528-1.). It is further well-known in the art that treatment therapy of type 1 hypersensitivity can involve adrenaline (epinephrine), antihistamines and corticosteroids.

Examples of type 1 hypersensitivity include allergic asthma, allergic conjunctivitis, allergic rhinitis (hay fever), anaphylaxis, angioedema, uriticaria (hives), eosinophilia, penicillin allergy, cephalosporin allergy, food allergy, and sweet itch.

"Treating an allergy" refers to treating a subject having allergy so that one or more allergy (e.g., type 1 hypersensitivity) symptoms are reduced, ameliorated, or eliminated. An "effective amount" of a therapeutic agent refers to the amount of the agent sufficient to result in amelioration of one or more symptoms of allergy ated in a statistically significant manner.

Symptoms of type 1 hypersensitivity include sneezing, stuffy or runny nose and eyes, itchy nose and throat, sometimes a nasal-sounding voice, difficulty breathing, poor appetite, snoring during sleep and coughing with or without phlegm associated with allergic rhinitis (commonly called hay fever); and severe dyspnoea, swelling of the bronchial mucosa and hypersecretion of mucus, leading to bronchial obstruction associated with Bronchial asthma. In further embodiments of the above method, the therapeutic agent or treatment comprises an antihistamine (e.g., fexofenadine, loratadine, and cetirizine), a mast cell stabilizer (e.g., sodium cromoglycate and lodoxamide tromethamine), a steroid (e.g., prednisolone and dexamethasone), cyclosporine, adrenaline, or immunotherapy (i.e., gradual sensitization of an individual towards a know antigen).

The therapeutic agent may be administered via a route appropriate for such an agent, including taken by mouth and local or topical administration.

In the following, the invention is explained with reference to the figures by means of examples. The embodiments described are to be understood in every respect solely as examples that are not limitative, and various combinations of the listed features are included in the scope of the invention.

BRIEF DESCRIPTION OF THE DRAWINGS

FIGS. 1A-1D). In each case, 50 μl of whole blood from a person allergic to pollen was stimulated with allergen extracts (t2: elder pollen extract; t3: birch pollen extract; t4: hazel pollen extract) in various concentrations (10 μg-1 ng) or controls (anti-FcεRI and fMLP), and basophil activation was determined by the chemiluminescence test. The respective bar charts show the absolute RLU measurement values depending on the allergen concentrations or the controls. The measurement values are also given above the bars. FIG. 1A shows the reaction of the unstimulated control (neg. ctrl.) and control stimulation with anti-FcεRI and fMLP. FIG. 1B shows the reaction of the samples stimulated with various concentrations (10 μg/ml, 1 μg/ml, 100 ng/ml, 10 ng/ml) of elder pollen extract. FIG. 1C shows the reaction of the samples stimulated with various concentrations (1 μg/ml, 100 ng/ml, 10 ng/ml, 1 ng/ml) of birch pollen extract. FIG. 1D shows the reaction of the samples stimulated with various concentrations (10 μg/ml, 1 μg/ml, 100 ng/ml, 10 ng/ml) of hazel pollen extract. Determination was carried out in triplicate. Mean values and standard deviations were calculated. FIGS. 1E-H shows the stimulation index (SI) calculated as (mean value of RLU of activated sample)/(mean value of RLU of neg. control) for the samples shown in FIGS. 1A-D.

FIGS. 2E-H). In each case, 50 μl of whole blood from a person allergic to pollen was stimulated with the same allergen extracts as in the test of FIGS. 1A-1H (t2: elder pollen extract; t3: birch pollen extract; t4: hazel pollen extract) in various concentrations (10 μg-1 ng) or controls (anti-FcεRI and fMLP), and basophil activation was determined by flow cytometry. The respective bar charts show the content of activated basophils depending on the allergen concentrations or the controls. The measurement values are also given above the bars. FIG. 2A shows the reaction of the unstimulated control (negative control) and control stimulation with anti-FcεRI and fMLP. Approx. 30% of the basophils were activated in both positive controls. At stimulation of greater than 10%, the reaction was evaluated as positive. FIG. 2B shows the reaction of the samples stimulated with various concentrations (10 μg/ml, 1 μg/ml, 100 ng/ml, 10 ng/ml) of elder pollen extract. FIG. 2C shows the reaction of the samples stimulated with various concentrations (1 μg/ml, 100 ng/ml, 10 ng/ml, 1 ng/ml) of birch pollen extract. FIG. 2D shows the reaction of the samples stimulated with various concentrations (10 μg/ml, 1 μg/ml, 100 ng/ml, 10 ng/ml) of hazel pollen extract. Cells with a CD123+/HLA-DR⁻ phenotype were identified as basophils, and activation was detected with anti-CD63-VioBlue.

The maximum reactivity of the basophils was 80-88% depending on the pollen extract at the respective highest concentration used and decreased steadily with increasing dilution of the allergen extracts.

Figure 1A:
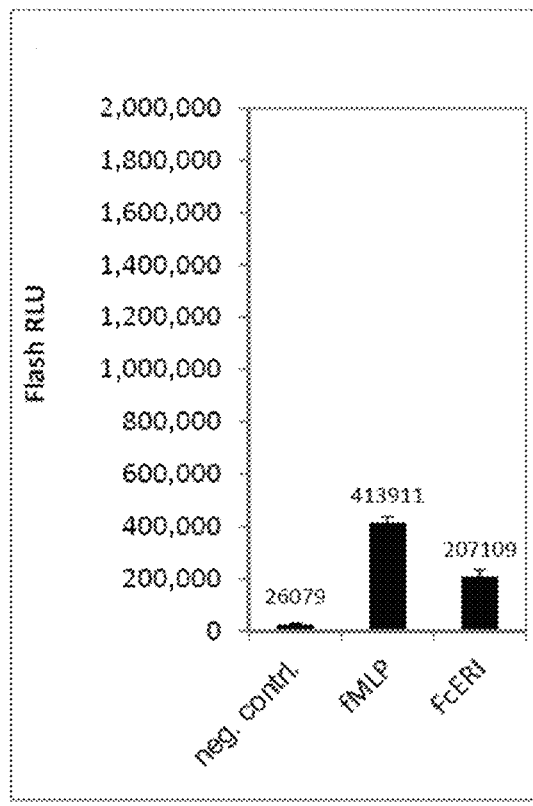
FIGS. 1A-1H shows the results of the method according to the invention measured in flash chemiluminescence relative light units (RLU.
Figure 1B:
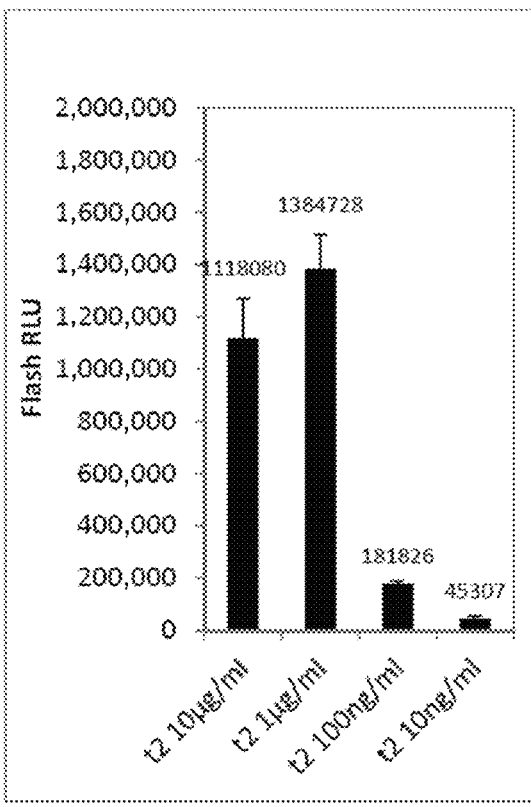
Figure 1C:
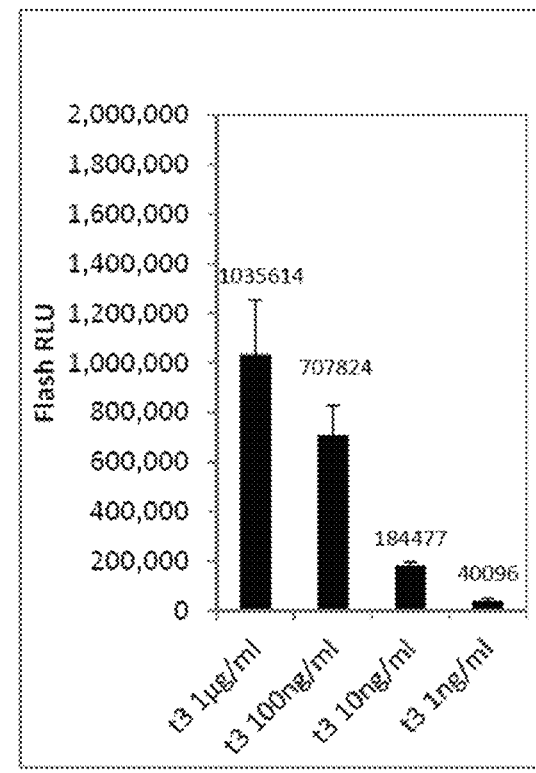
Figure 1D:
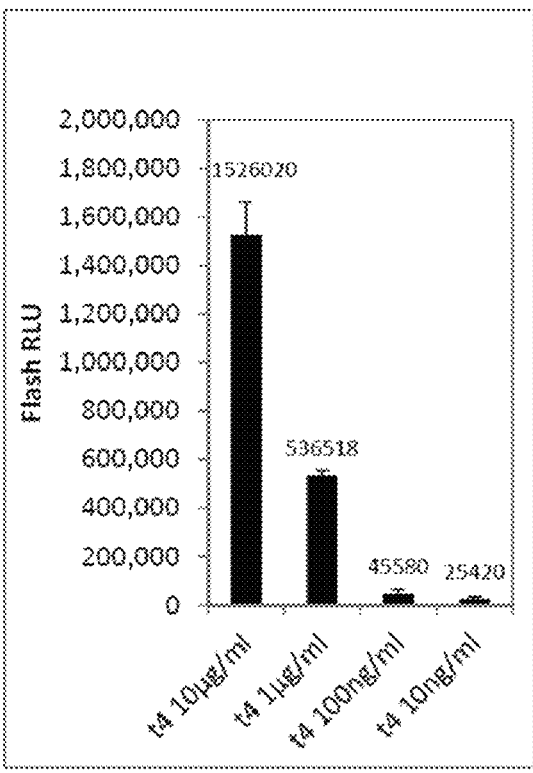
Figure 1E:
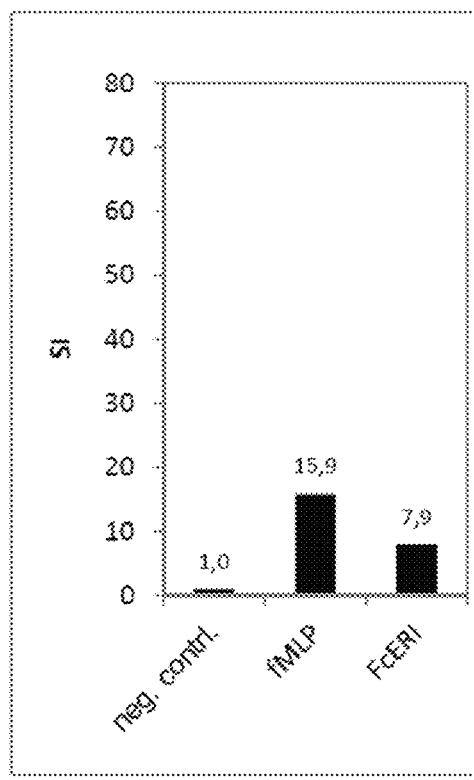
Figure 1F:
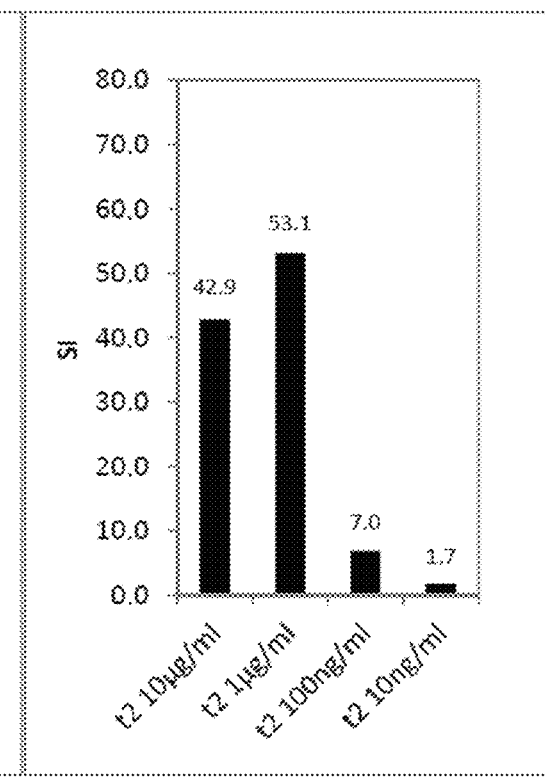
Figure 1G:
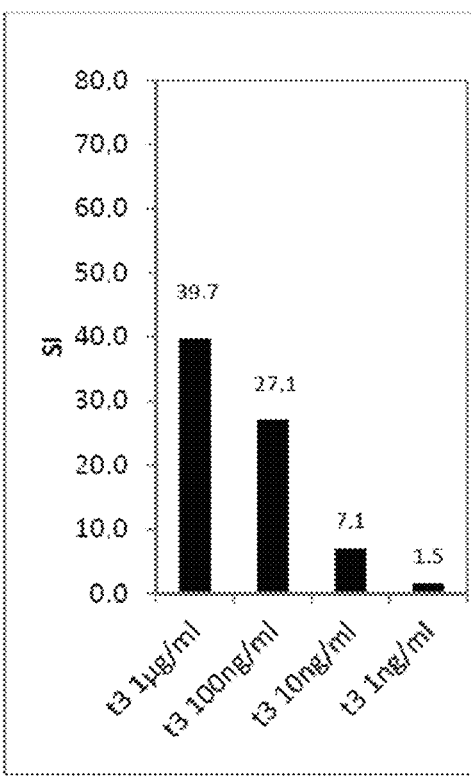
Figure 1H:
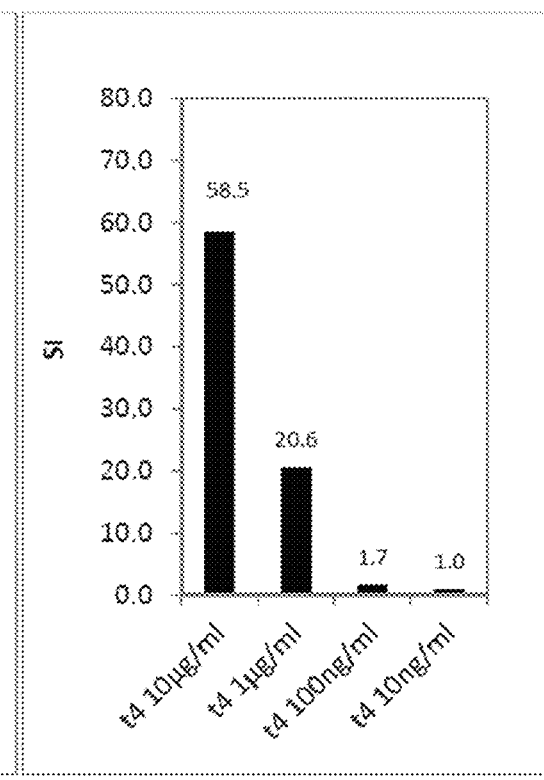
Figure 2A:
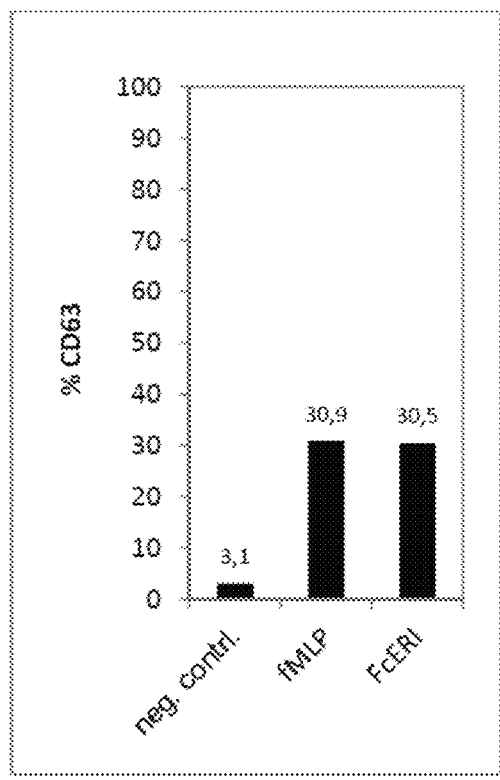
FIGS. 2A-2H shows a basophil activation test with flow cytometric determination of the activated basophils in % (FIGS. 2A-D) or as mean fluorescence intensity (MFI.
Figure 2B:
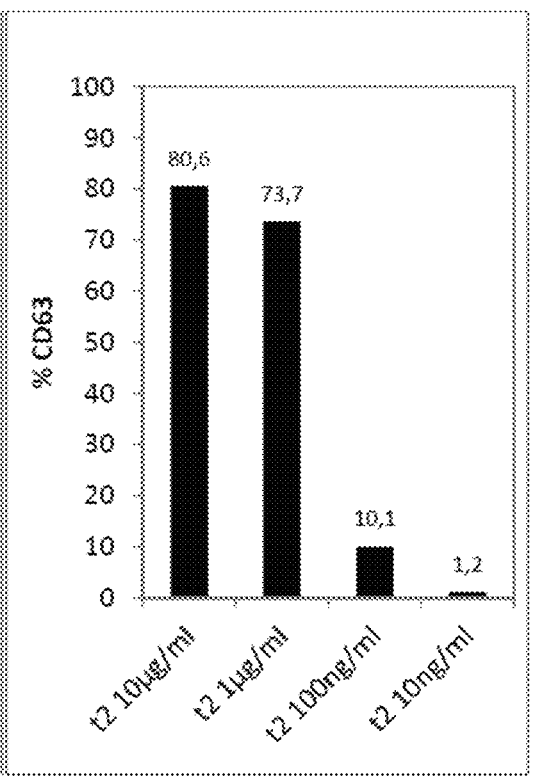
Figure 2C:
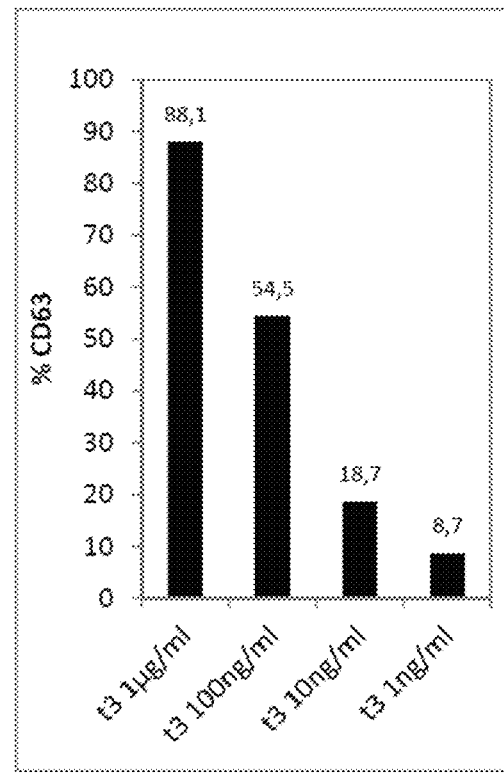
Figure 2D:
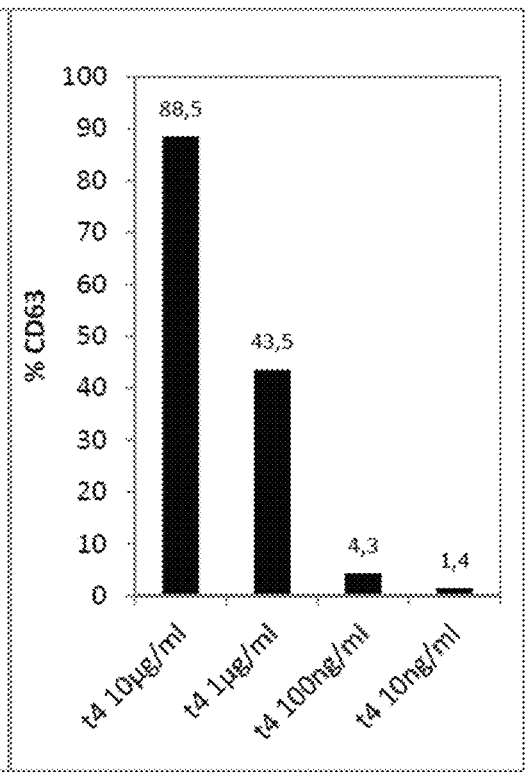
Figure 2E:
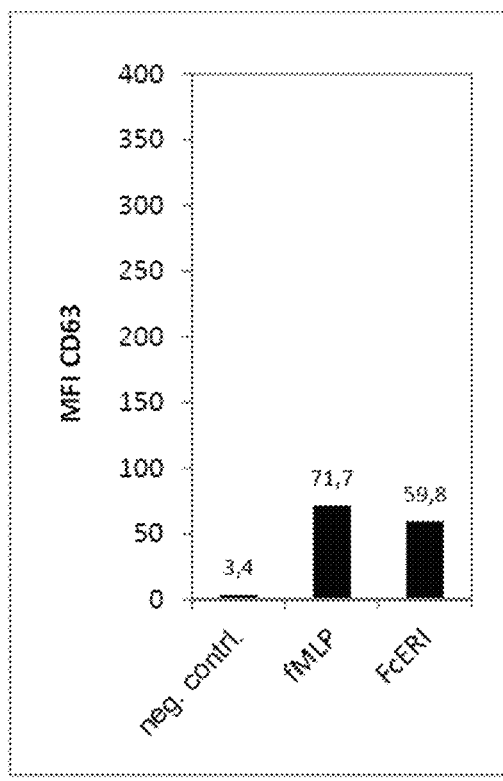
Figure 2F:
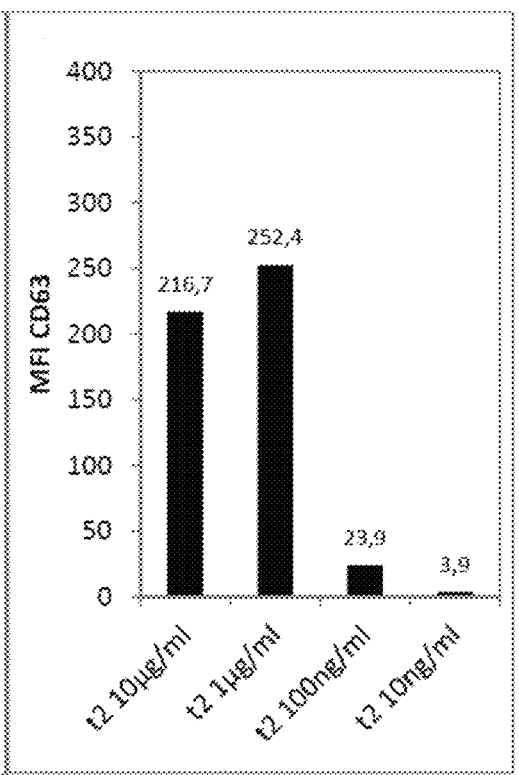
Figure 2G:
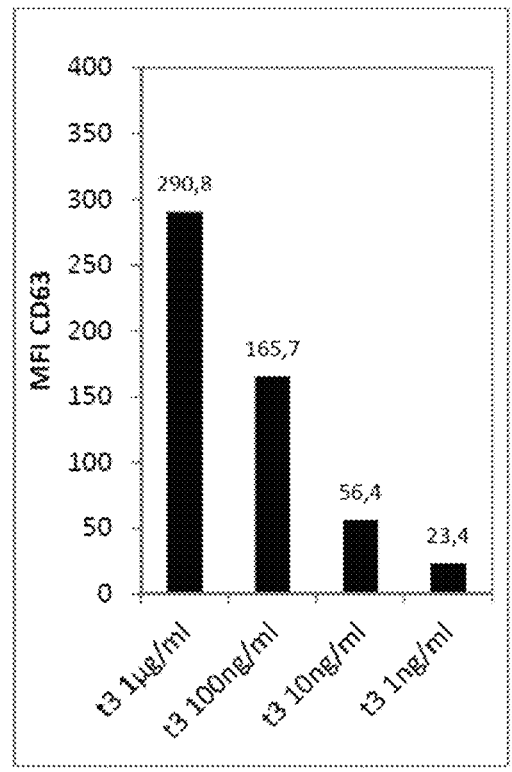
Figure 2H:
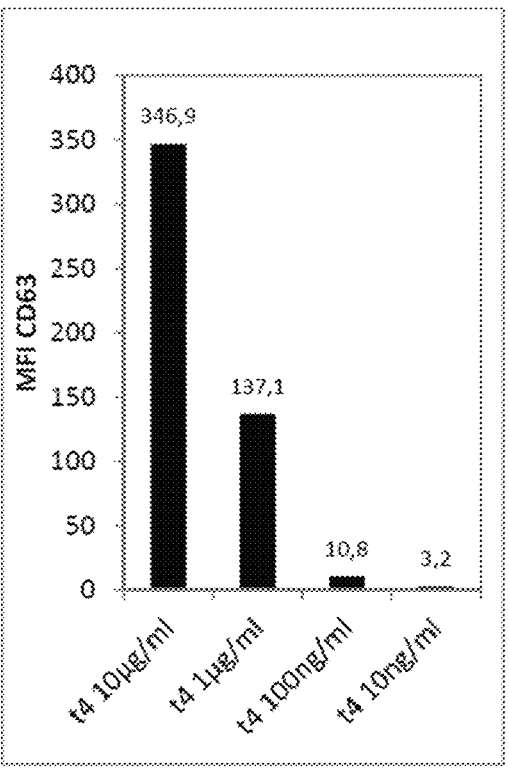
Figure 3A:
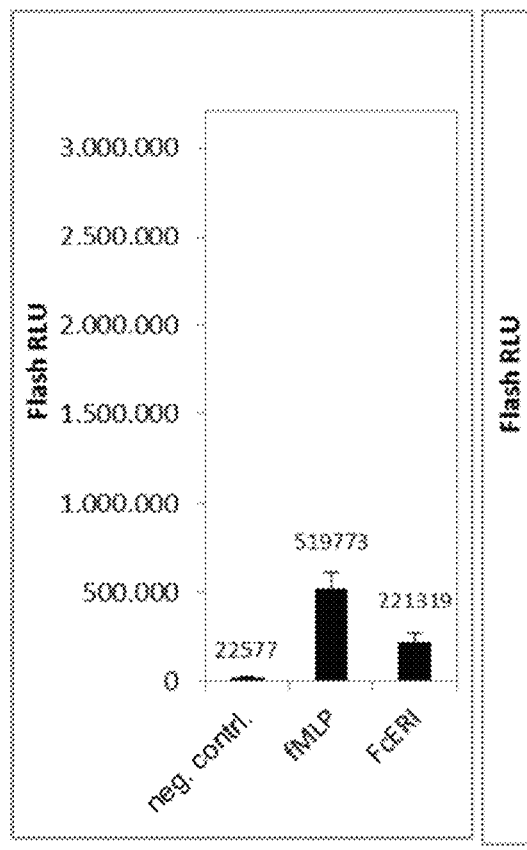
Figure 3B:
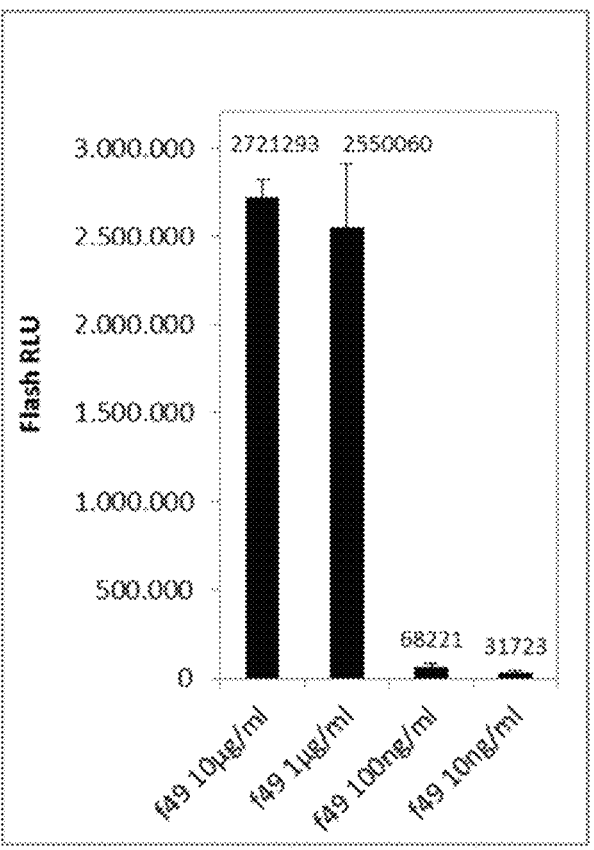
Figure 3C:
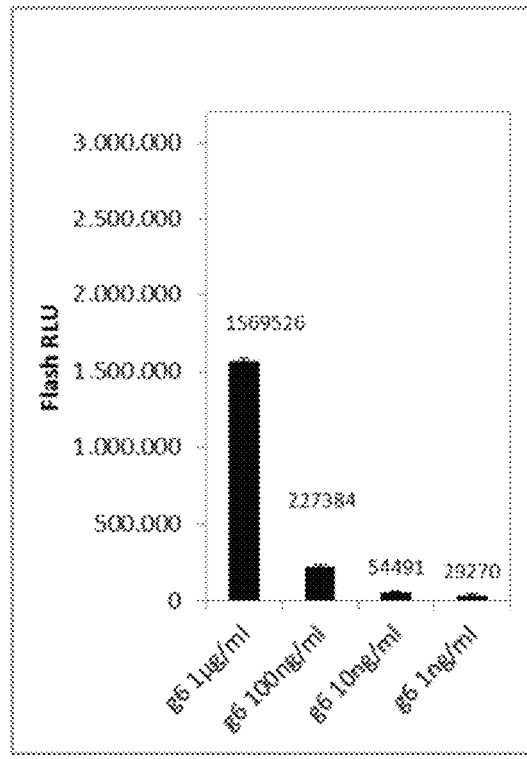
Figure 3D:
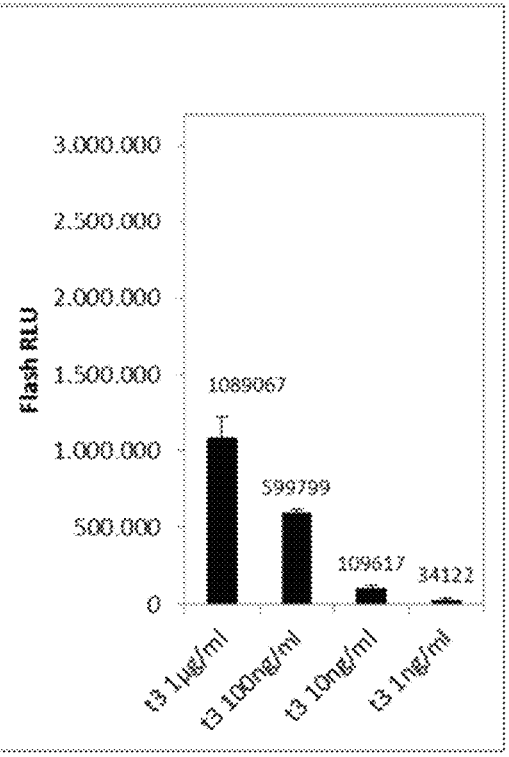

FIGS. 3A-3H shows the results of the method according to the invention measured in flash chemiluminescence relative light units (RLU; FIGS. 3A-D). In each case, 50 μl of whole blood from a person allergic to pollen was stimulated with allergen extracts (f49: apple extract; g6: timothy grass pollen extract; t3: birch pollen extract) in various concentrations (10 μg-1 ng) or controls (anti-FcεRI and fMLP), and basophil activation was determined by the chemiluminescence test. The respective bar charts show the absolute RLU measurement values depending on the allergen concentrations or the controls. The measurement values are also given above the bars. FIG. 3A shows the reaction of the unstimulated control (neg. ctrl.) and control stimulation with anti-FcεRI and fMLP. FIG. 3B shows the reaction of the samples stimulated with various concentrations (10 μg/ml, 1 μg/ml, 100 ng/ml, 10 ng/ml) of apple extract. FIG. 3C shows the reaction of the samples stimulated with various concentrations (1 μg/ml, 100 ng/ml, 10 ng/ml, 1 ng/ml) of timothy grass pollen extract. FIG. 3D shows the reaction of the samples stimulated with various concentrations (1 μg/ml, 100 ng/ml, 10 ng/ml, 1 ng/ml) of birch pollen extract. Determination was carried out in triplicate. Mean values and standard deviations were calculated. FIGS. 3E-H shows the stimulation index (SI) calculated as (mean value of RLU of activated sample)/(mean value of RLU of neg. control) for the samples shown in FIGS. 3A-D.

Figure 4A:
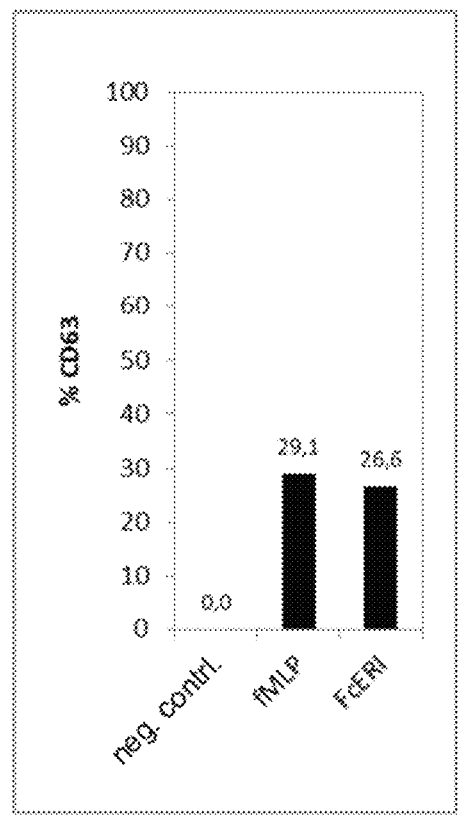
Figure 4B:
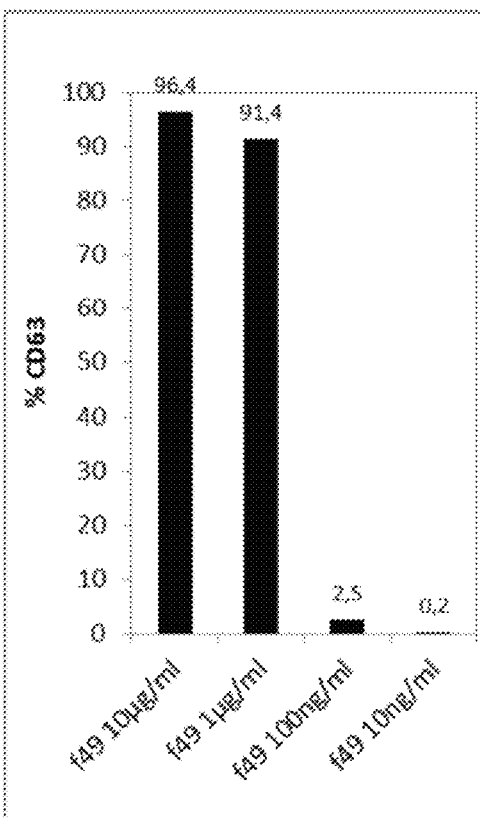
Figure 4C:
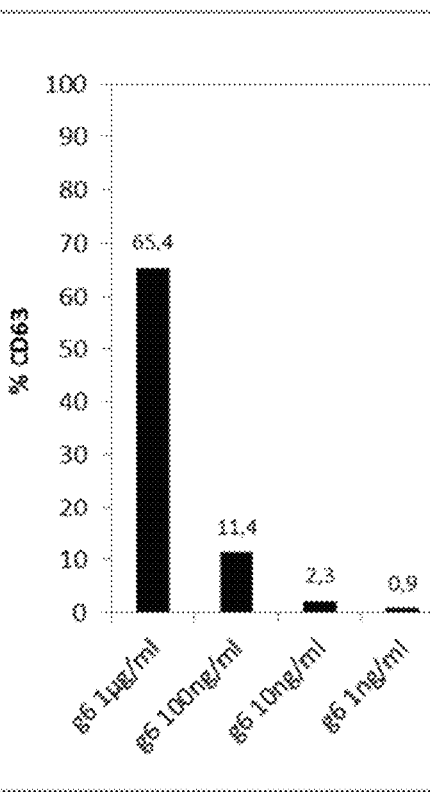
Figure 4D:
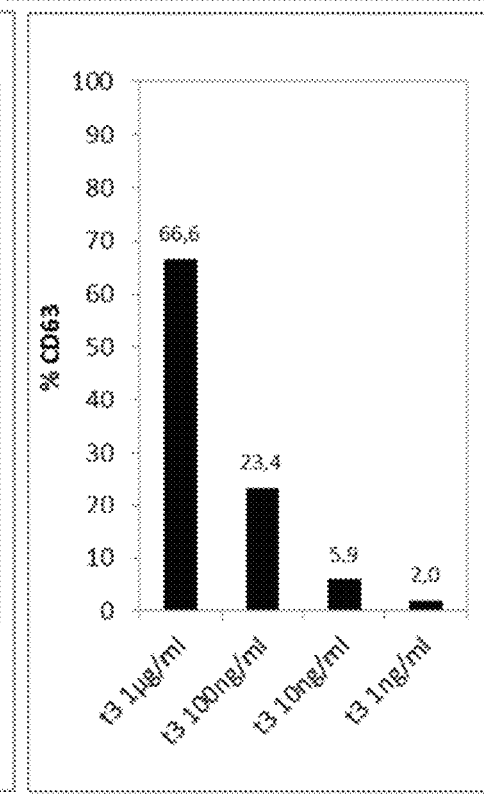

FIGS. 4A-4H shows a basophil activation test with flow cytometric determination of the activated basophils in % (FIGS. 4A-D) or as mean fluorescence intensity (MFI; FIGS. 4E-H). In each case, 50 μl of whole blood from a person allergic to pollen was stimulated with allergen extracts (f49: apple extract; g6: timothy grass pollen extract; t3: birch pollen extract) in various concentrations (10 μg-1 ng) or controls (anti-FcεRI and fMLP) and basophil activation was determined by flow cytometry. The respective bar charts show the content of activated basophils depending on the allergen concentrations or the controls. The measurement values are also given above the bars. FIG. 4A shows the reaction of the unstimulated control (negative control) and control stimulation with anti-FcεRI and fMLP. Approx. 30% of the basophils were activated in both positive controls. At stimulation of greater than 10%, the reaction was evaluated as positive. FIG. 4B shows the reaction of the samples stimulated with various concentrations (10 μg/ml, 1 μg/ml, 100 ng/ml, 10 ng/ml) of apple extract. FIG. 4C shows the reaction of the samples stimulated with various concentrations (1 μg/ml, 100 ng/ml, 10 ng/ml, 1 ng/ml) of timothy grass pollen extract. FIG. 4D shows the reaction of the samples stimulated with various concentrations (1 μg/ml, 100 ng/ml, 10 ng/ml, 1 ng/ml) of birch pollen extract. Cells with a CD123+/HLA-DR⁻ phenotype were identified as basophils, and activation was detected with anti-CD63-VioBlue.

Depending on the extract, the maximum reactivity of the basophils was 96-65% at the respective highest concentration used and decreased steadily with increasing dilution of the allergen extracts.

Figure 5A:
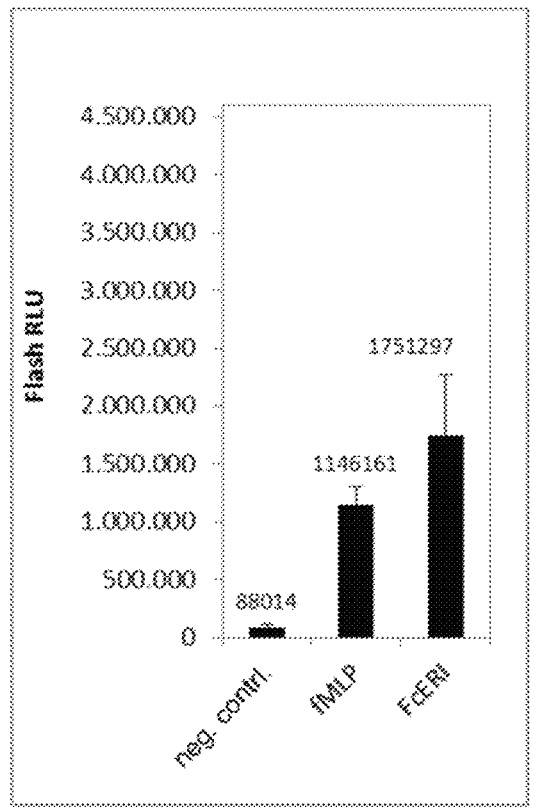
Figure 5B:
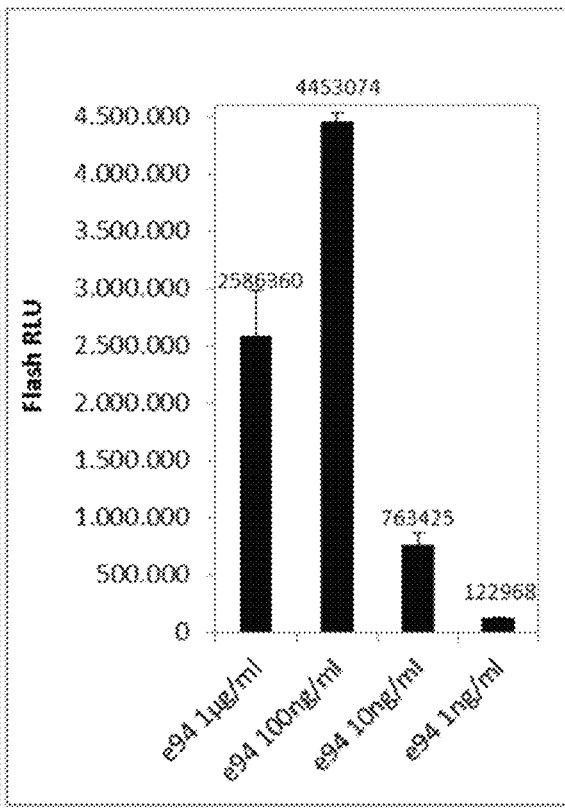
Figure 5C:
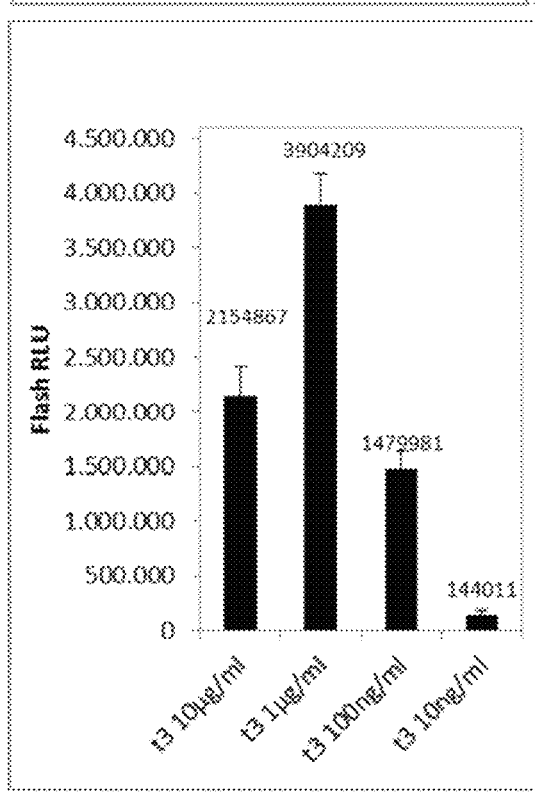
Figure 5D:
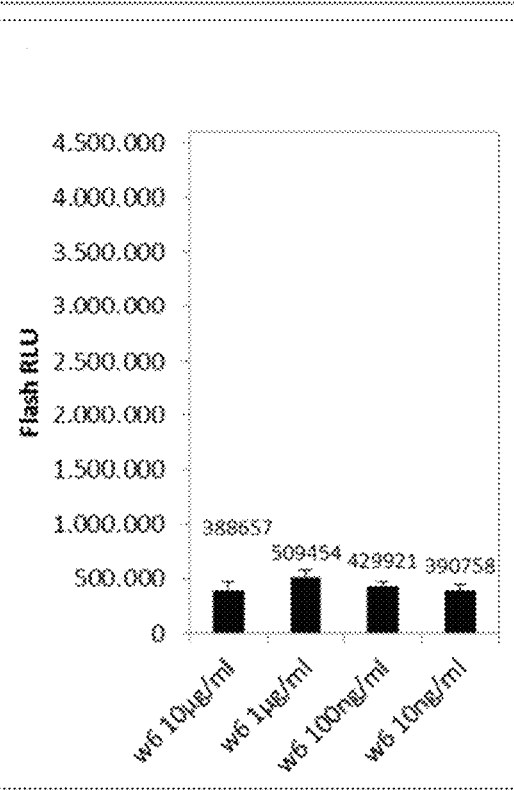
Figure 5E:
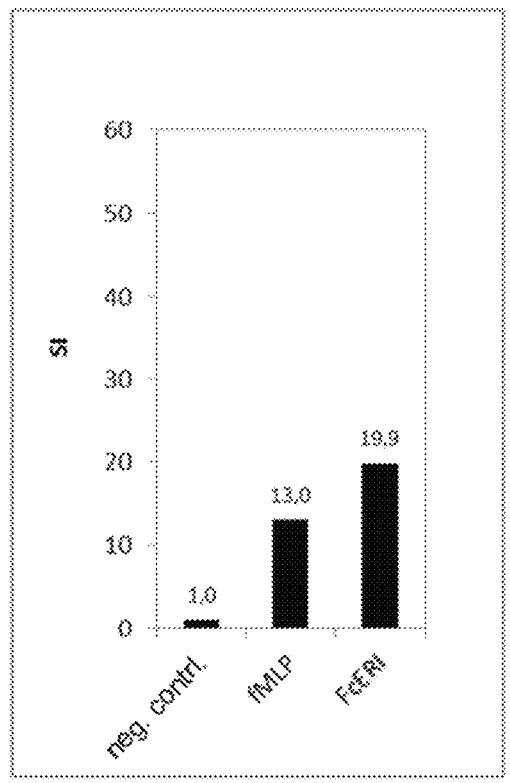
Figure 5F:
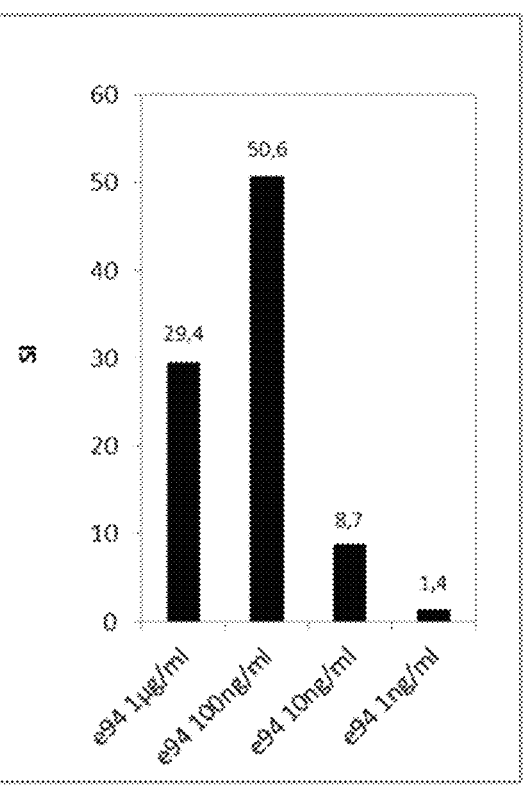
Figure 5G:
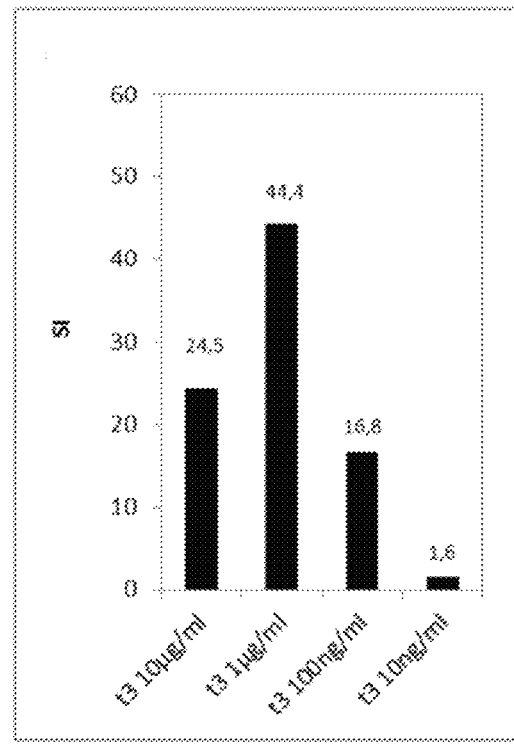
Figure 5H:
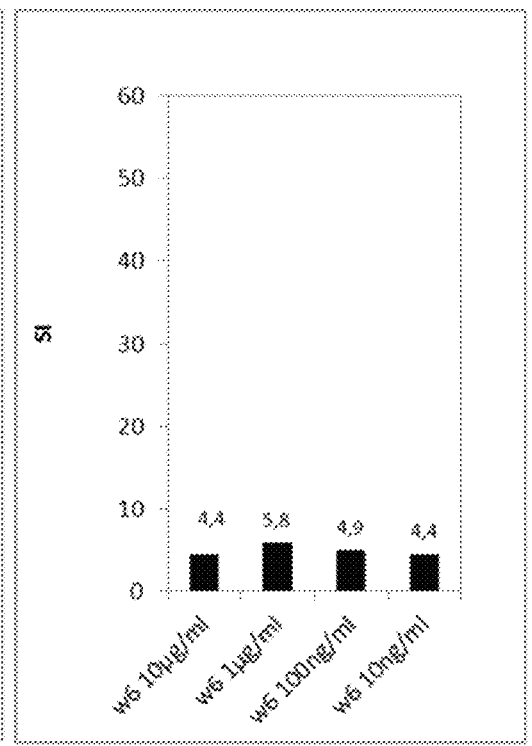

FIGS. 5A-5H shows the results of the method according to the invention measured in flash chemiluminescence relative light units (RLU; FIGS. 5A-D). In each case, 50 μl of whole blood from a person allergic to pollen was stimulated with allergen extracts (e94: rFeld d 1; t3: birch pollen extract; w6: mugwort pollen extract) in various concentrations (10 μg-1 ng) or controls (anti-FcεRI and fMLP), and basophil activation was determined by the chemiluminescence test. The respective bar charts show the absolute RLU measurement values depending on the allergen concentrations or the controls. The measurement values are also given above the bars. FIG. 5A shows the reaction of the unstimulated control (neg. ctrl.) and control stimulation with anti-FcεRI and fMLP. FIG. 5B shows the reaction of the samples stimulated with various concentrations (1 μg/ml, 100 ng/ml, 10 ng/ml, 1 ng/ml) of rFel d 1. FIG. 5C shows the reaction of the samples stimulated with various concentrations (10 μg/ml, 1 μg/ml, 100 ng/ml, 10 ng/ml) of birch pollen extract. FIG. 5D shows the reaction of the samples stimulated with various concentrations (10 μg/ml, 1 μg/ml, 100 ng/ml, 10 ng/ml) of mugwort pollen extract. Determination was carried out in triplicate. Mean values and standard deviations were calculated. FIGS. 5E-H shows the stimulation index (SI) calculated as (mean value of RLU of activated sample)/(mean value of RLU of neg. control) for the samples shown in FIGS. 5A-D.

Figure 6A:
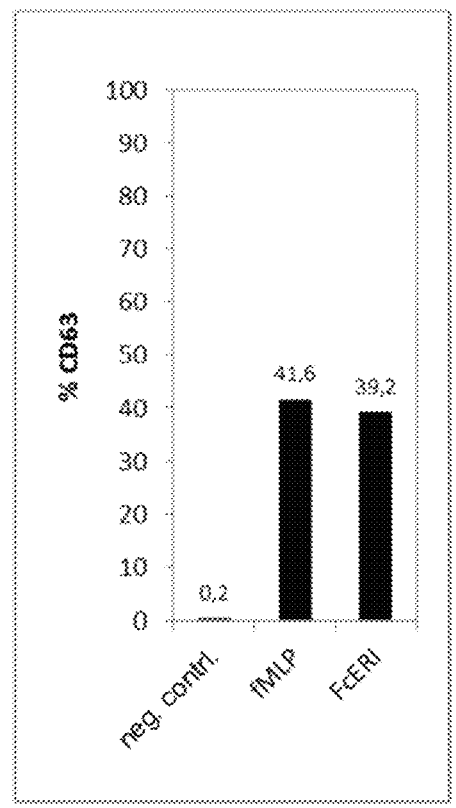
Figure 6B:
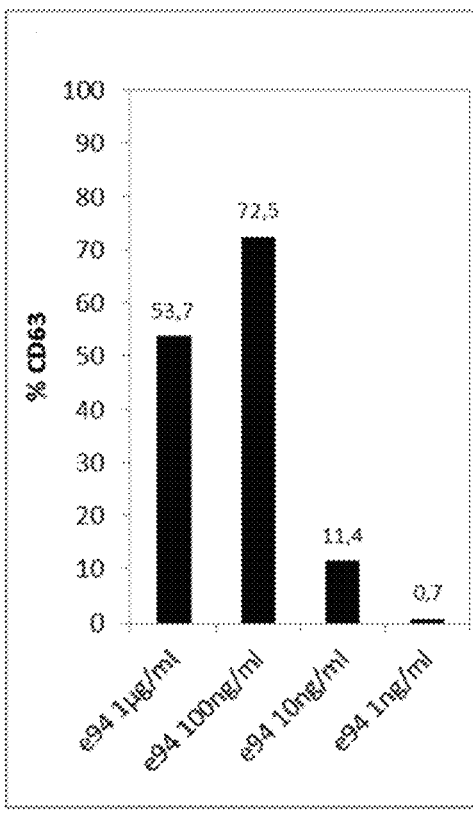
Figure 6C:
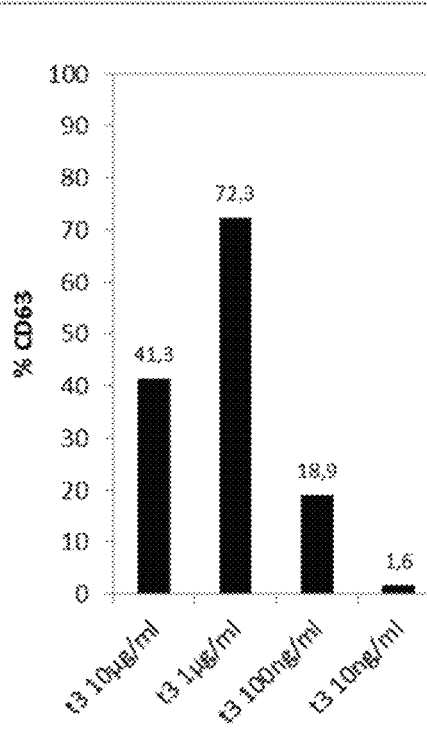
Figure 6D:
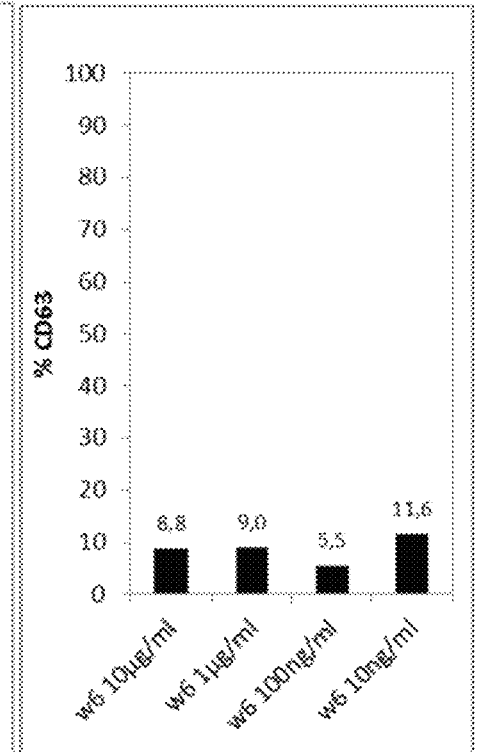

FIGS. 6A-6H shows a basophil activation test with flow cytometric determination of the activated basophils in % (FIG. 6A-D) or as mean fluorescence intensity (MFI; FIGS. 6E-H). In each case, 50 μl of whole blood from a person allergic to pollen was stimulated with allergen extracts (e94: rFeld d 1; t3: birch pollen extract; w6: mugwort pollen extract) in various concentrations (10 μg-1 ng) or controls (anti-FcεRI and fMLP) and basophil activation was determined by flow cytometry. The respective bar charts show the content of activated basophils depending on the allergen concentrations or the controls. The measurement values are also given above the bars. FIG. 6A shows the reaction of the unstimulated control (negative control) and control stimulation with anti-FcεRI and fMLP. Approx. 40% of the basophils were activated in both positive controls. At stimulation of greater than 10%, the reaction was evaluated as positive. FIG. 6B shows the reaction of the samples stimulated with various concentrations (1 μg/ml, 100 ng/ml, 10 ng/ml, 1 ng/ml) of rFel d 1. FIG. 6C shows the reaction of the samples stimulated with various concentrations (10 μg/ml, 1 μg/ml, 100 ng/ml, 10 ng/ml) of birch pollen extract. FIG. 6D shows the reaction of the samples stimulated with various concentrations (10 μg/ml, 1 μg/ml, 100 ng/ml, 10 ng/ml) of mugwort pollen extract. Cells with a CD123+/HLA-DR⁻ phenotype were identified as basophils, and activation was detected with anti-CD63-VioBlue.

Depending on the extract, the maximum reactivity of the basophils was 73-12%.

Figure 7A:
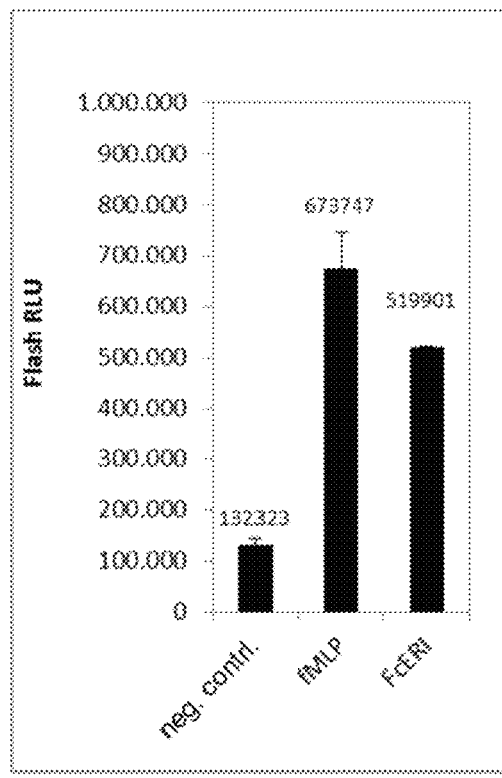
Figure 7B:
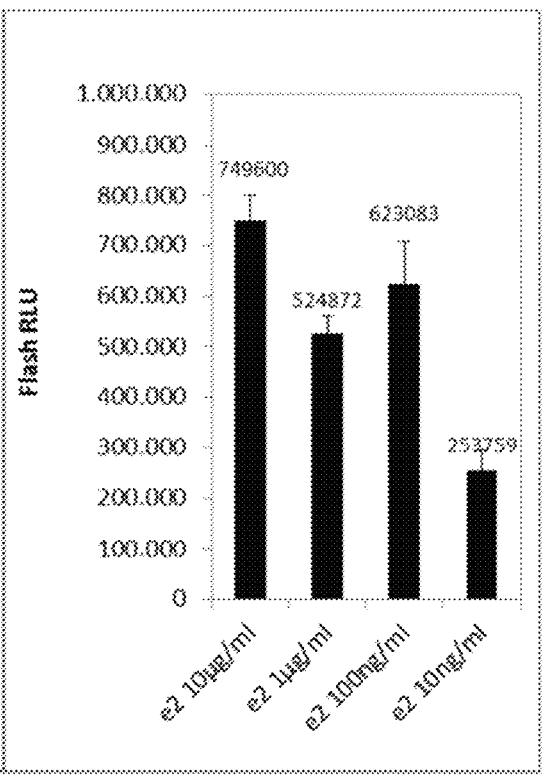
Figure 7B:
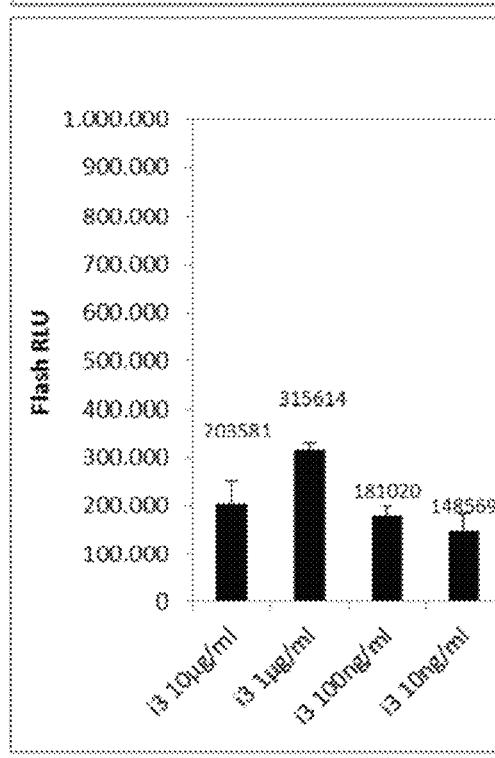
Figure 7B:
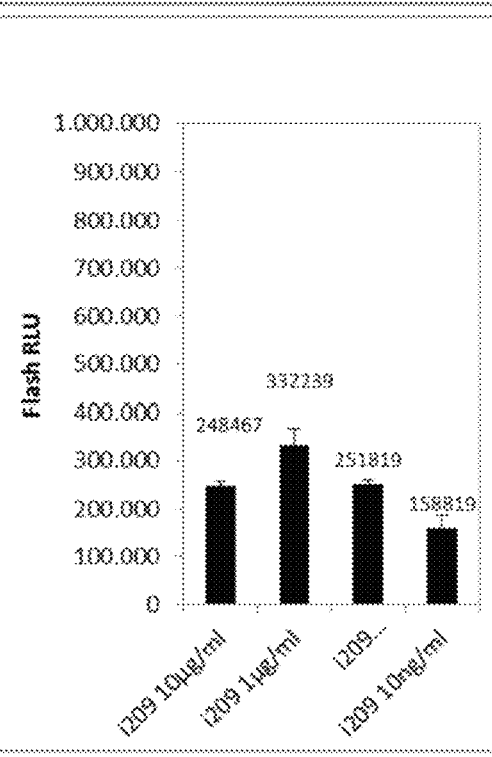
Figure 7E:
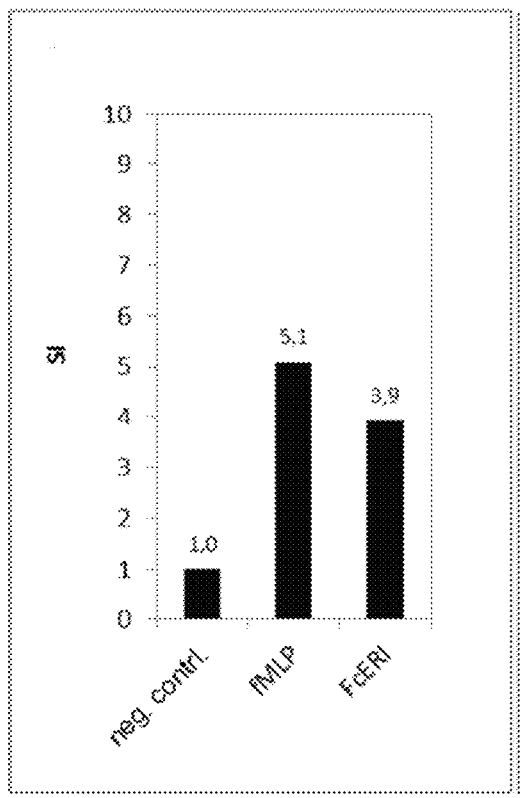
Figure 7F:
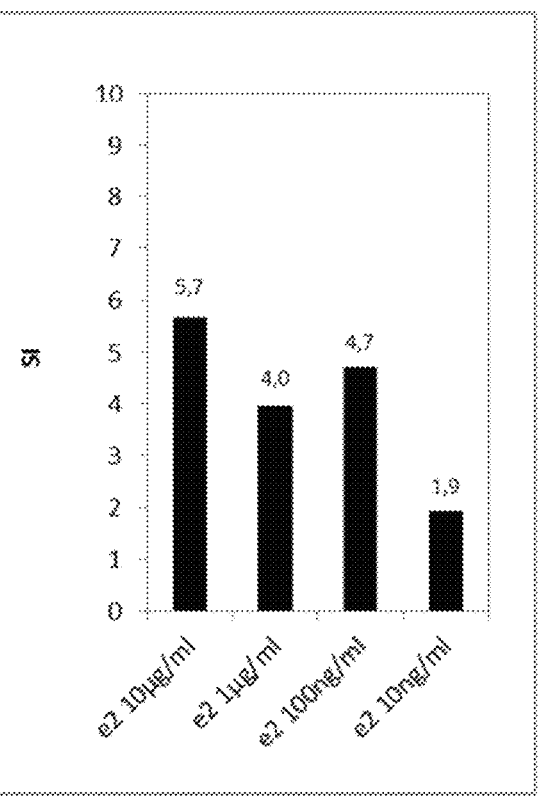
Figure 7G:
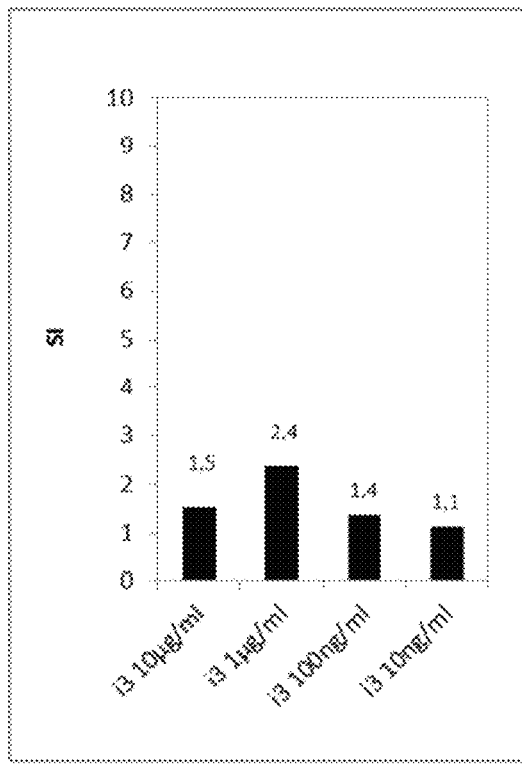
Figure 7H:
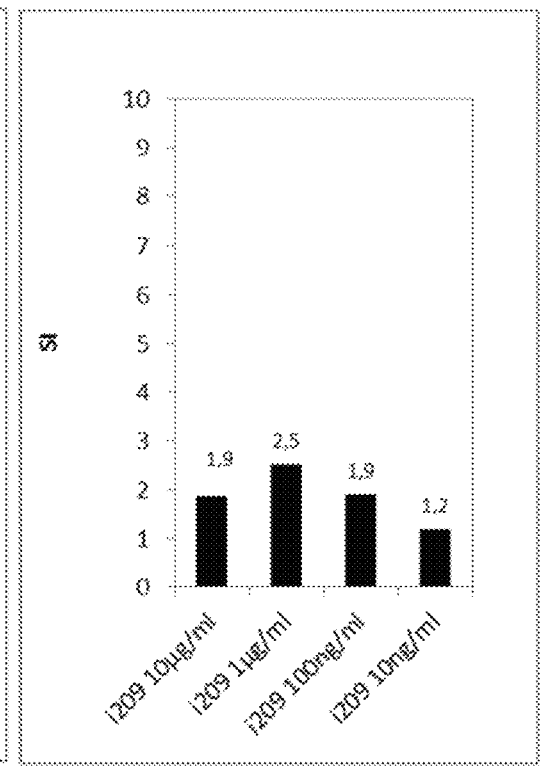

FIGS. 7A-7H shows the results of the method according to the invention measured in flash chemiluminescence relative light units (RLU; FIGS. 7A-D). In each case, 50 μl of whole blood from a person allergic to pollen was stimulated with allergen extracts (e2: dog hair extract; i3: wasp venom extract; i209: rVes v 5) in various concentrations (10 μg-1 ng) or controls (anti-FcεRI and fMLP), and basophil activation was determined by the chemiluminescence test. The respective bar charts show the absolute RLU measurement values depending on the allergen concentrations or the controls. The measurement values are also given above the bars. FIG. 7A shows the reaction of the unstimulated control (neg. ctrl.) and control stimulation with anti-FcεRI and fMLP. FIG. 7B shows the reaction of the samples stimulated with various concentrations (10 μg/ml, 1 μg/ml, 100 ng/ml, 10 ng/ml) of dog hair extract. FIG. 7C shows the reaction of the samples stimulated with various concentrations (10 μg/ml, 1 μg/ml, 100 ng/ml, 10 ng/ml) of wasp venom extract. FIG. 7D shows the reaction of the samples stimulated with various concentrations (10 μg/ml, 1 μg/ml, 100 ng/ml, 10 ng/ml) of rVes v 5. Determination was carried out in triplicate. Mean values and standard deviations were calculated. FIGS. 7E-H shows the stimulation index (SI) calculated as (mean value of RLU of activated sample)/(mean value of RLU of neg. control) for the samples shown in FIGS. 7A-D.

Figure 8A:
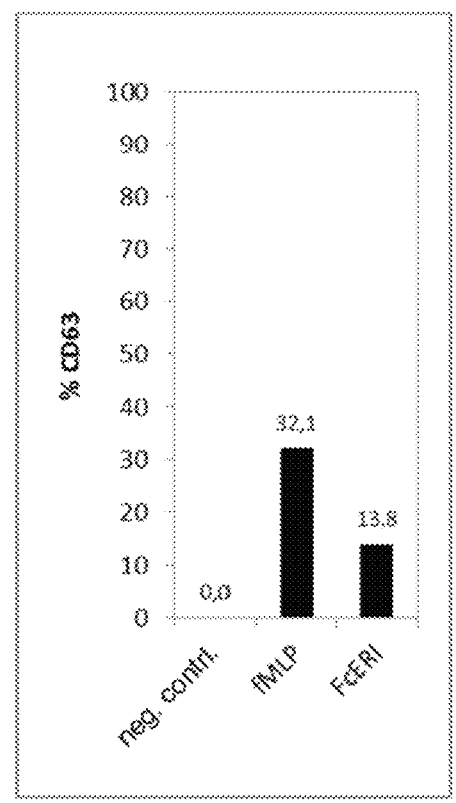
Figure 8B:
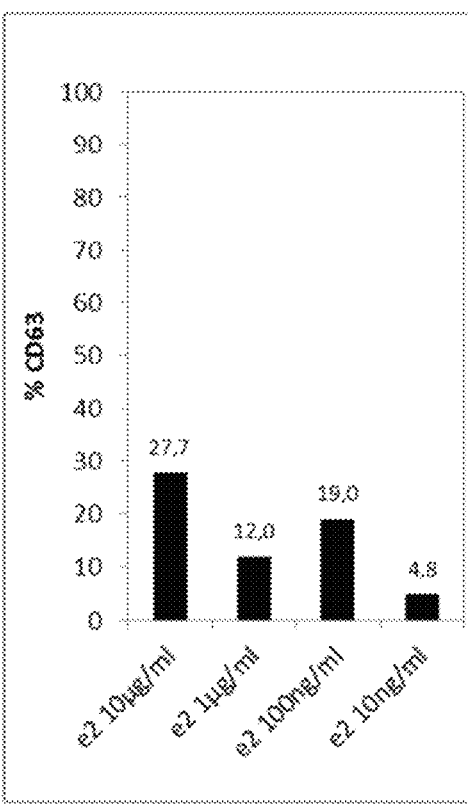
Figure 8C:
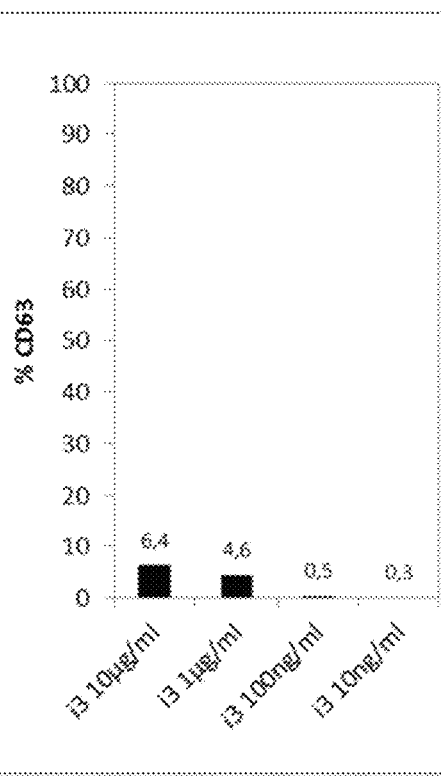
Figure 8D:
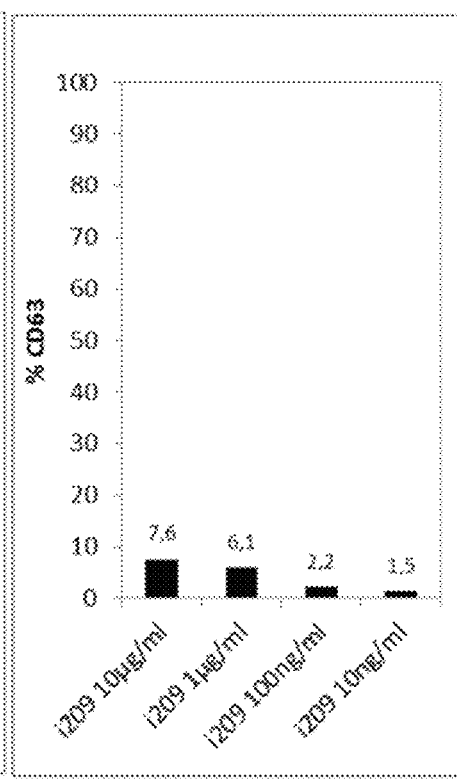

FIGS. 8A-8H shows a basophil activation test with flow cytometric determination of the activated basophils in % (FIGS. 8A-D) or as mean fluorescence intensity (MFI; FIGS. 8E-H). In each case, 50 μl of whole blood from a person allergic to pollen was stimulated with allergen extracts (e2: dog hair extract; i3: wasp venom extract; i209: rVes v 5) in various concentrations (10 μg-1 ng) or controls (anti-FcεRI and fMLP) and basophil activation was determined by flow cytometry. The respective bar charts show the content of activated basophils depending on the allergen concentrations or the controls. The measurement values are also given above the bars. FIG. 8A shows the reaction of the unstimulated control (negative control) and control stimulation with anti-FcεRI and fMLP. Approx. 30% of the basophils were activated in both positive controls. At stimulation of greater than 10%, the reaction was evaluated as positive. FIG. 8B shows the reaction of the samples stimulated with various concentrations (1 µg/ml, 100 ng/ml, 10 ng/ml, 1 ng/ml) of dog hair extract. FIG. 8C shows the reaction of the samples stimulated with various concentrations (1 µg/ml, 100 ng/ml, 10 ng/ml, 1 ng/ml) of wasp venom extract. FIG. 8D shows the reaction of the samples stimulated with various concentrations (10 µg/ml, 1 µg/ml, 100 ng/ml, 10 ng/ml) of rVes v 5. Cells with a CD123+/HLA-DR− phenotype were identified as basophils, and activation was detected with anti-CD63-VioBlue.

Depending on the extract, the maximum reactivity of the basophils was 25-8%.

Figure 9A:
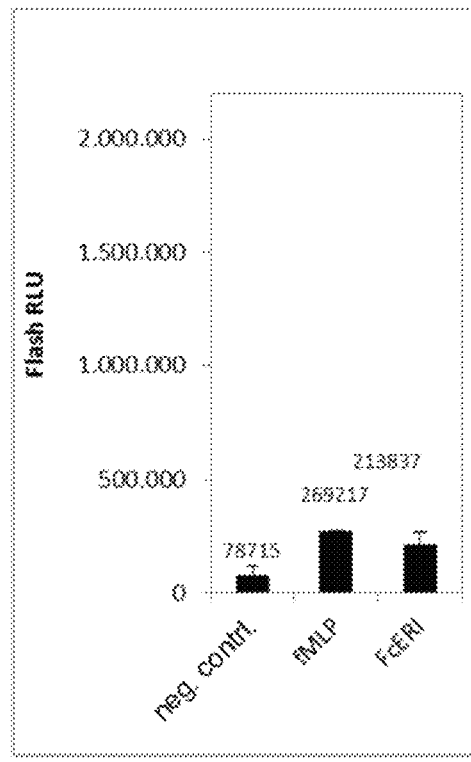

FIGS. 9A-9J shows the results of the method according to the invention measured in flash chemiluminescence relative light units (RLU; FIGS. 9A-D). In each case, 50 µl of whole blood from a person allergic to pollen was stimulated with allergen extracts (w8: dandelion pollen extract; f17: hazelnut extract; f49: apple extract; e94 rFel d 1) in various concentrations (10 µg-100 ng) or controls (anti-FcεRI and fMLP), and basophil activation was determined by the chemiluminescence test. The respective bar charts show the absolute RLU measurement values depending on the allergen concentrations or the controls. The measurement values are also given above the bars. FIG. 9A shows the reaction of the unstimulated control (neg. ctrl.) and control stimulation with anti-FcεRI and fMLP.

Figure 9B:
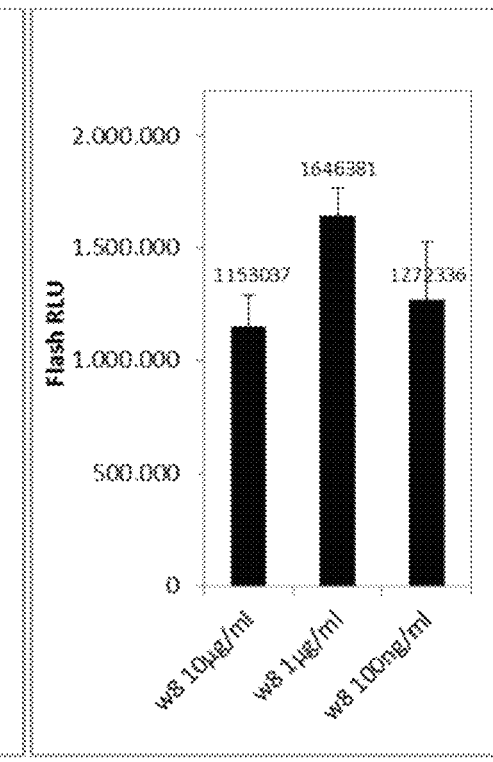
Figure 9C:
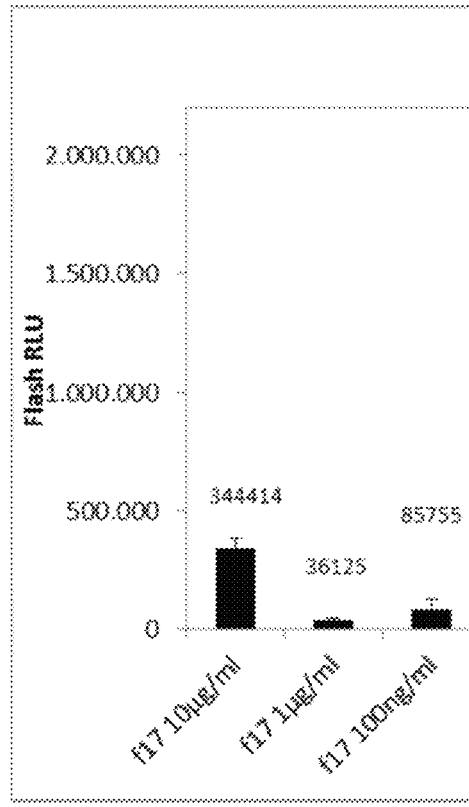
Figure 9D:
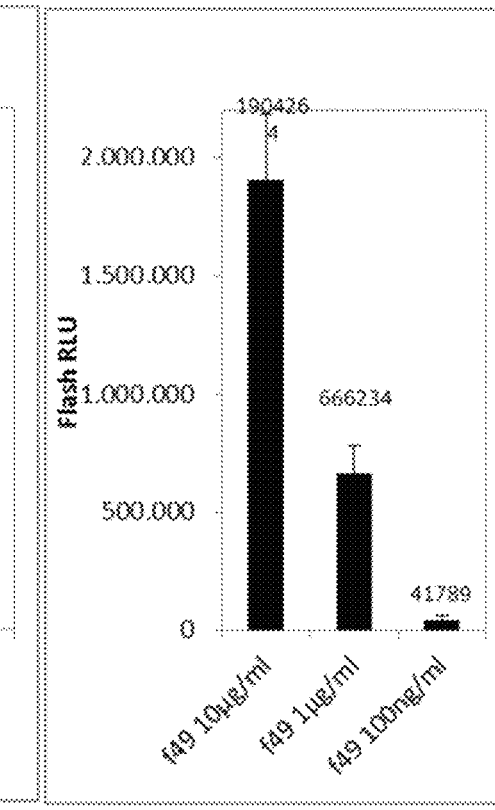
Figure 9I:
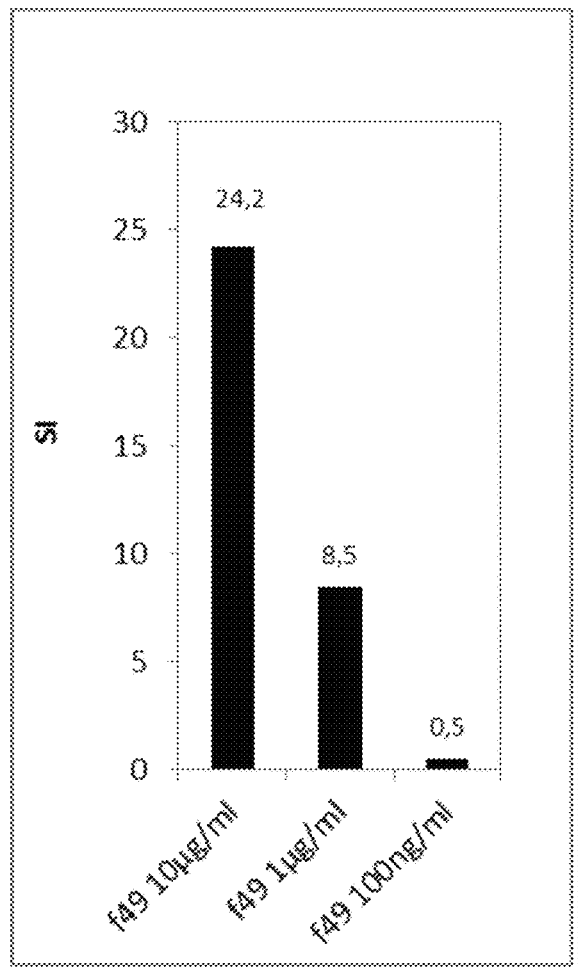
Figure 9J:
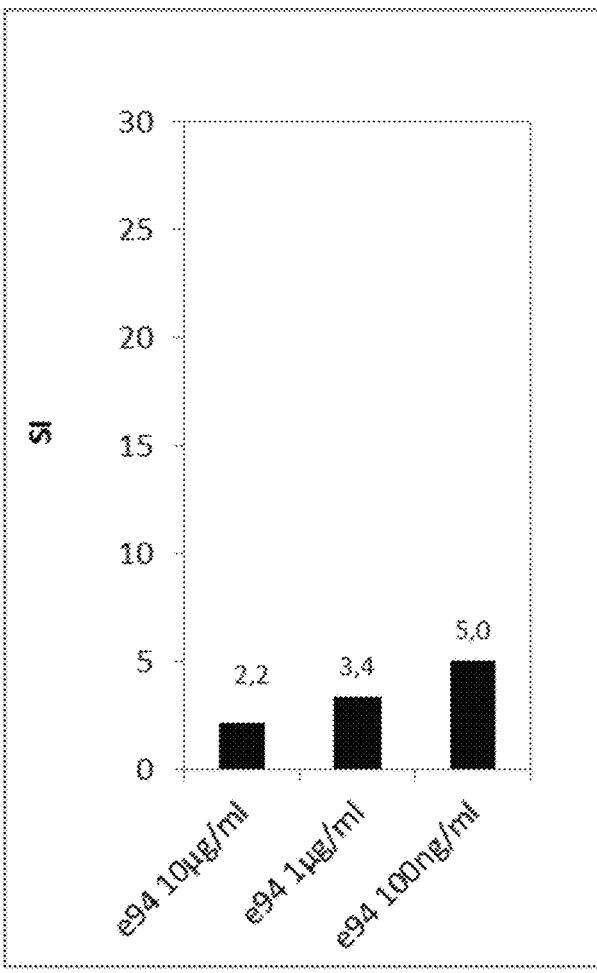

FIG. 9B shows the reaction of the samples stimulated with various concentrations (10 µg/ml, 1 µg/ml, 100 ng/ml) of dandelion pollen extract. FIG. 9C shows the reaction of the samples stimulated with various concentrations (10 µg/ml, 1 µg/ml, 100 ng/ml) of hazelnut extract. FIG. 9D shows the reaction of the samples stimulated with various concentrations (10 µg/ml, 1 µg/ml, 100 ng/ml) of apple extract. FIG. 9E shows the reaction of the samples stimulated with various concentrations (10 µg/ml, 1 µg/ml, 100 ng/ml) of rFel d 1. Determination was carried out in triplicate. Mean values and standard deviations were calculated. FIGS. 9F-J shows the stimulation index (SI) calculated as (mean value of RLU of activated sample)/(mean value of RLU of neg. control) for the samples shown in FIGS. 9A-E.

Figure 10A:
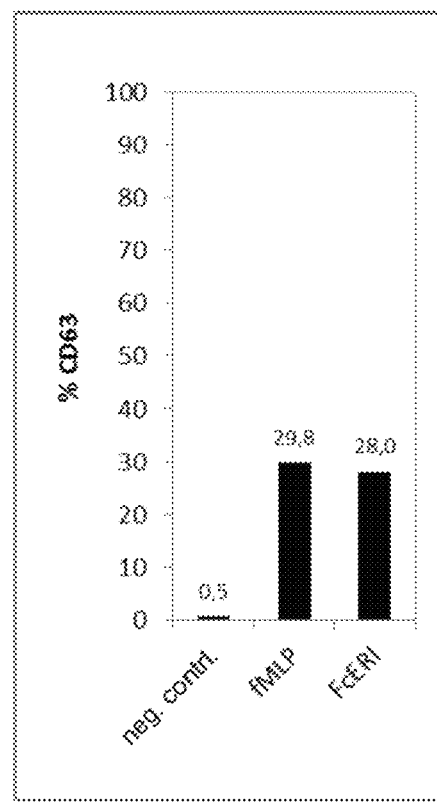
Figure 10B:
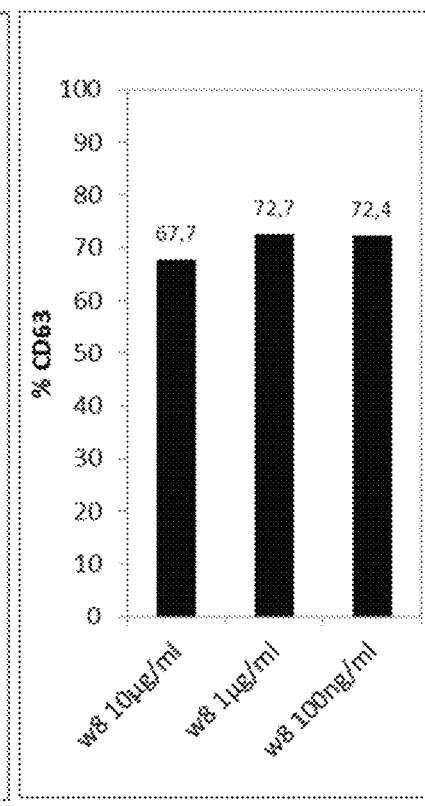
Figure 10C:
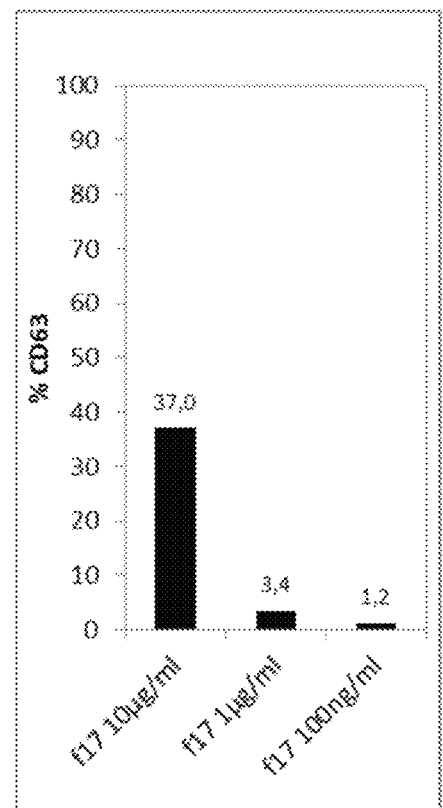
Figure 10D:
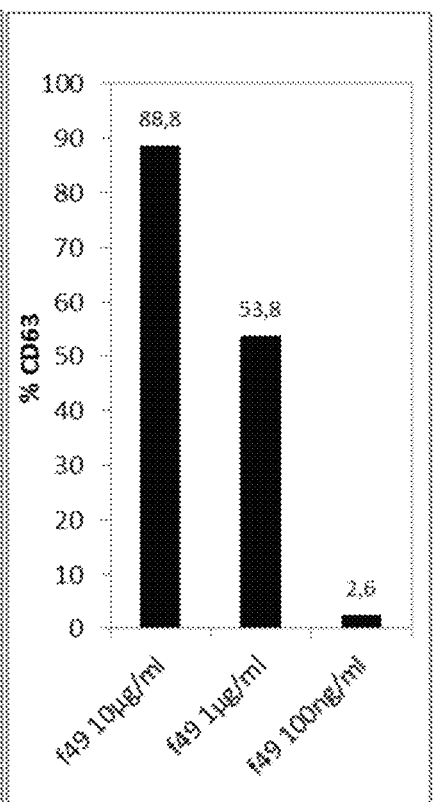
Figure 10I:
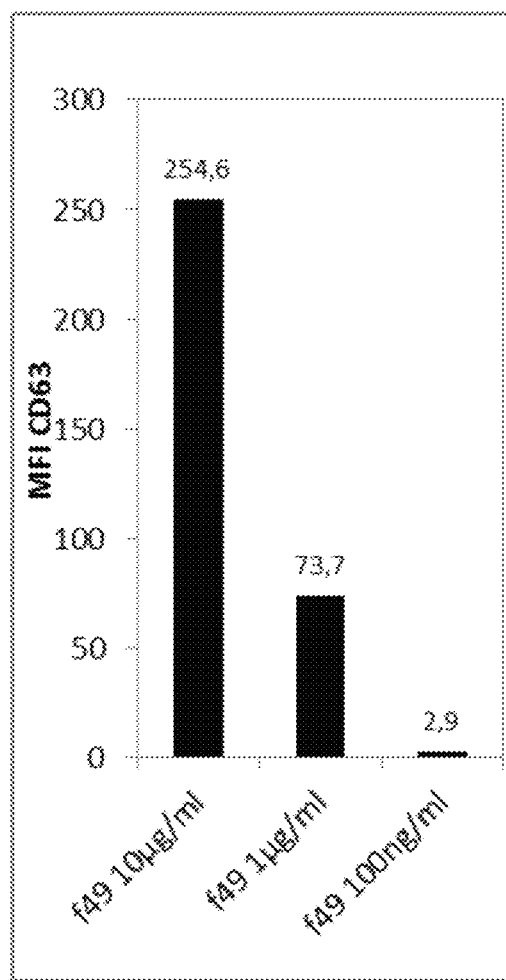
Figure 10J:
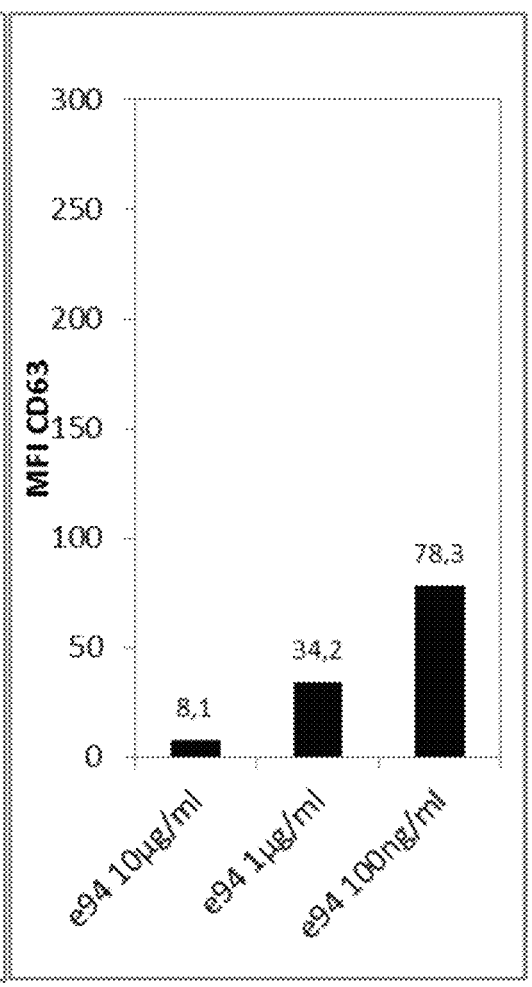

FIGS. 10A-10J shows a basophil activation test with flow cytometric determination of the activated basophils in % (FIGS. 10A-E) or as mean fluorescence intensity (MFI; FIGS. 10F-J). In each case, 50 µl of whole blood from a person allergic to pollen was stimulated with allergen extracts (w8: dandelion pollen extract; f17: hazelnut extract; f49: apple extract; e94 rFel d 1) in various concentrations (10 µg-100 ng) or controls (anti-FcεRI and fMLP) and basophil activation was determined by flow cytometry. The respective bar charts show the content of activated basophils depending on the allergen concentrations or the controls. The measurement values are also given above the bars. FIG. 10A shows the reaction of the unstimulated control (negative control) and control stimulation with anti-FcεRI and fMLP. Approx. 30% of the basophils were activated in both positive controls. At stimulation of greater than 10%, the reaction was evaluated as positive. FIG. 10B shows the reaction of the samples stimulated with various concentrations (10 µg/ml, 1 µg/ml, 100 ng/ml) of dandelion pollen extract. FIG. 10C shows the reaction of the samples stimulated with various concentrations (10 µg/ml, 1 µg/ml, 100 ng/ml) of hazelnut extract. FIG. 10D shows the reaction of the samples stimulated with various concentrations (10 µg/ml, 1 µg/ml, 100 ng/ml) of apple extract. FIG. 10E shows the reaction of the samples stimulated with various concentrations (10 µg/ml, 1 µg/ml, 100 ng/ml) of rFel d 1. Cells with a CD123+/HLA-DR− phenotype were identified as basophils, and activation was detected with anti-CD63-VioBlue.

Depending on the extract, the maximum reactivity of the basophils was 89-37%.

Figures 11A, 11B:
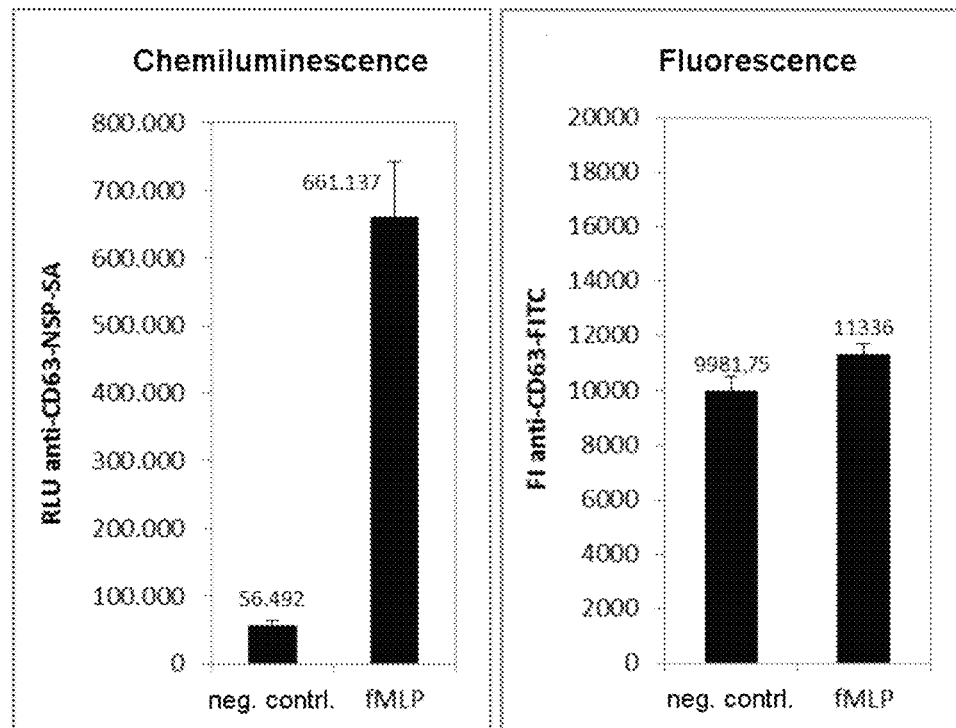
Figure 11C:
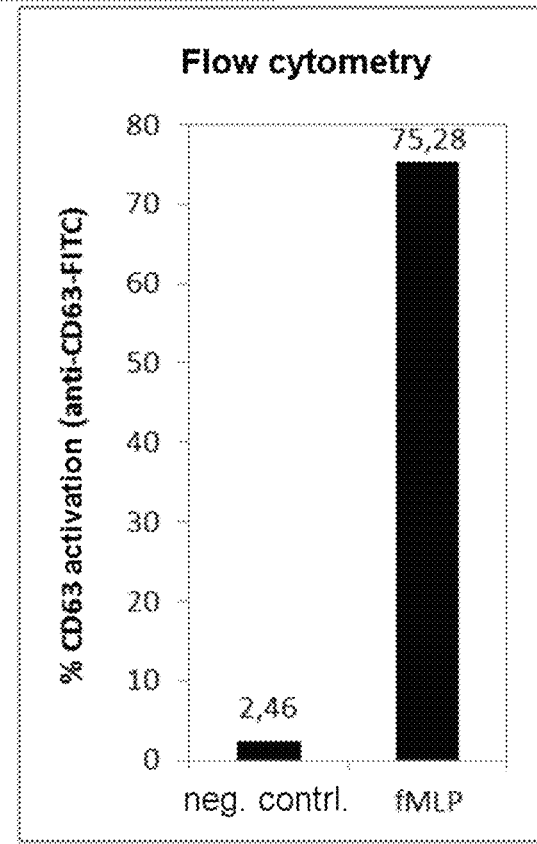

FIGS. 11A-11C shows the results of a patient sample after stimulation with fMLP of the unstimulated control (neg. ctrl.) with different detection systems. FIG. 11A shows the results of the method according to the invention measured in flash chemiluminescence relative light units (RLU). FIG. 11B shows the results of activation of basophils carried out according to the method of the invention after detection with a fluorescence-labeled antibody (anti-CD63-FITC; 2 µg/ml) measured as fluorescence intensity (FI). FIG. 11C shows a basophil activation test with flow cytometric determination of the activated basophils. In each case, 50 µl of whole blood from a person allergic to pollen was stimulated with fMLP or left unstimulated (neg. ctrl.). Basophil activation was then determined by the method described above. The respective bar charts show absolute measurement values in RLU (FIG. 11A) or FI (FIG. 11B) or basophil activation in % (FIG. 11C).

Figure 12D:
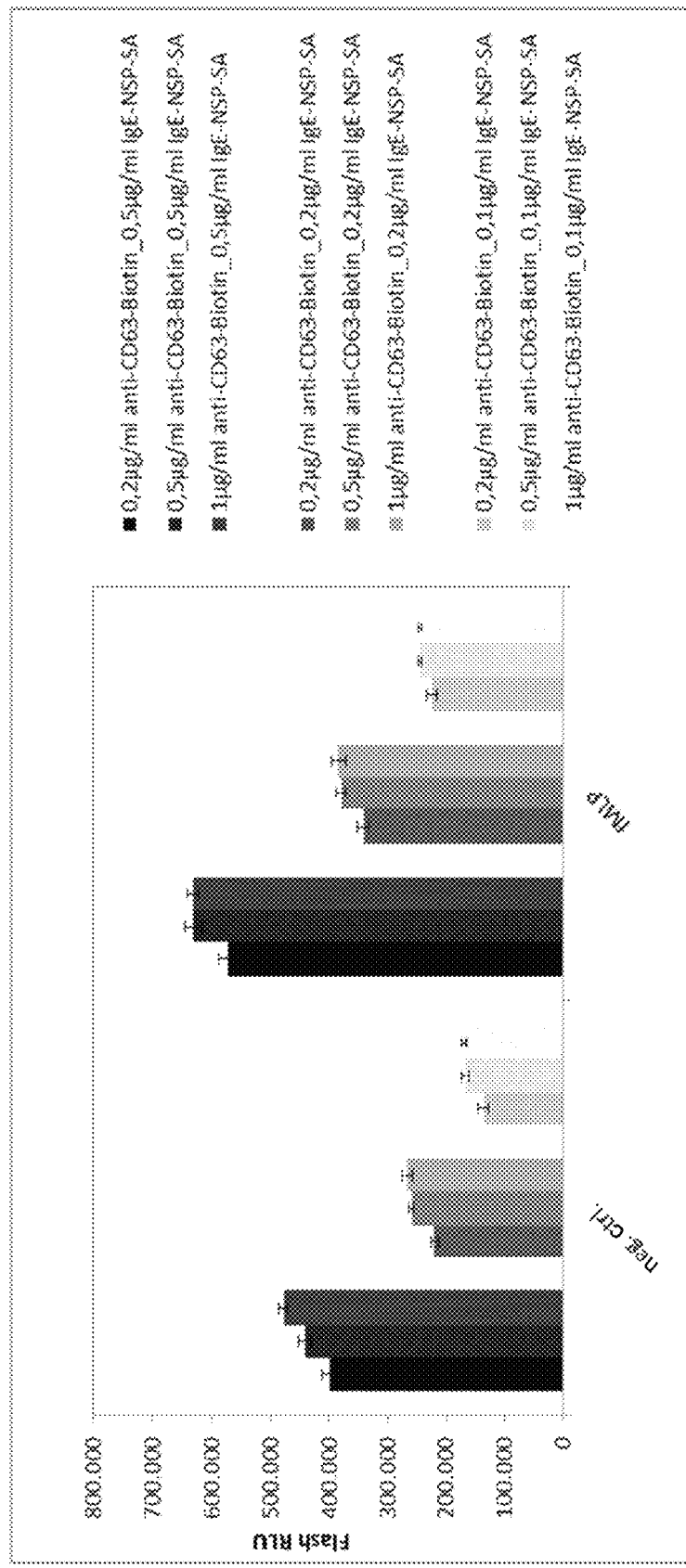
Figure 12E:
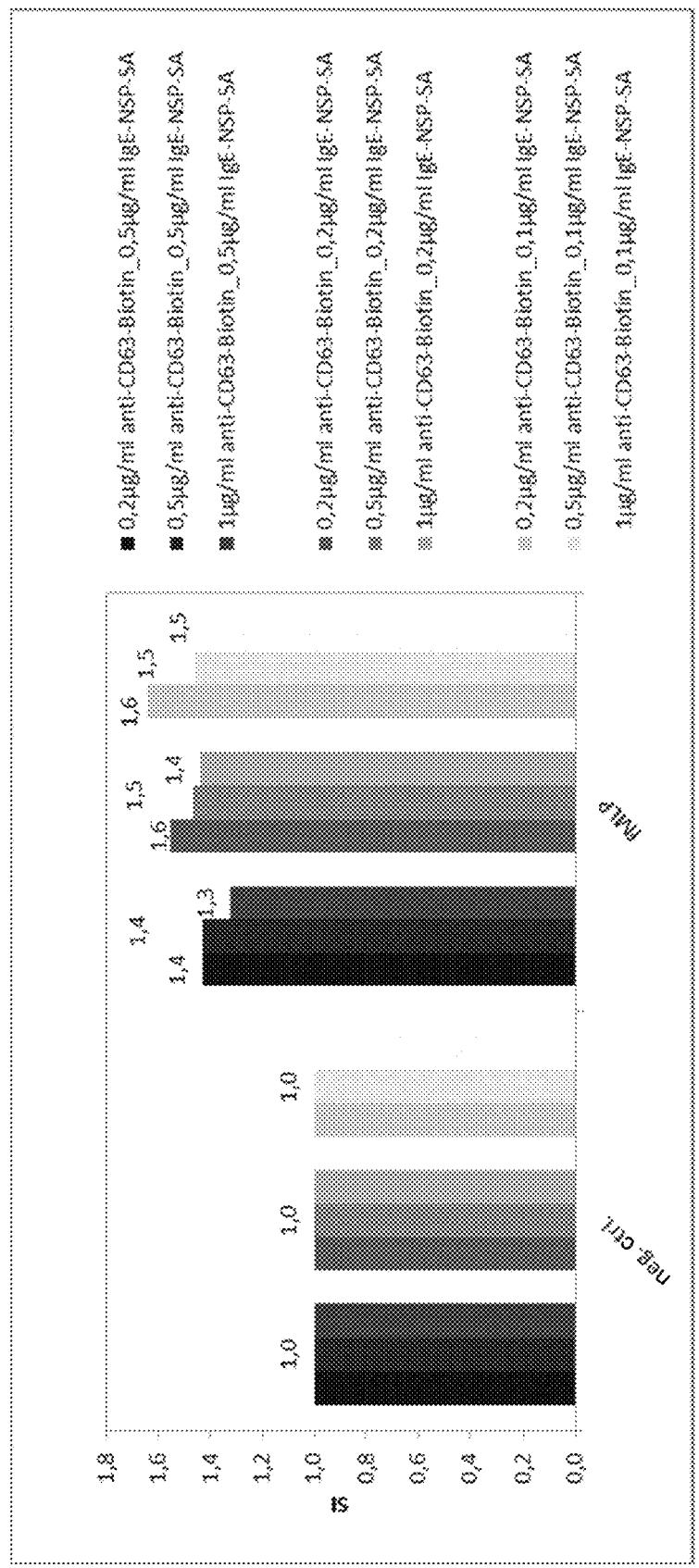

FIGS. 12A-12E shows the results of a patient sample after stimulation with fMLP or the unstimulated control (neg. ctrl.) using various antibody combinations for enrichment and detection of the basophils. No allergen was used. FIG. 12A shows the results of the method according to the invention measured in flash chemiluminescence relative light units (RLU). FIG. 12B shows the stimulation index (SI) calculated as (mean value of RLU of activated sample)/(mean value of RLU of neg. control) for the samples shown in FIG. 12A. FIG. 12C shows a basophil activation test with flow cytometric determination of the activated basophils. FIG. 12D shows the results of enrichment of the basophils with the activation-dependent marker CD63 via anti-CD63 biotin and detection with anti-IgE-NSP-SA. The anti-CD63 biotin antibody was used in concentrations of 0.2-1 µg/ml, while the detection antibody anti-IgE-NSP-SA was used in a fixed concentration of 0.5 µg/ml. FIG. 12E shows the stimulation index (SI) calculated as (mean value of RLU of activated sample)/(mean value of RLU of neg. control) for the samples shown in FIG. 12D.

EXAMPLES

1a. Preparation of Allergen Dilutions:

In order to detect basophil activation, an anti-CD63 antibody (Klon 7G3, BD Bioscience #353014) was covalently coupled to an NSP-SA-NHS acridinium ester (Heliosense Biotechnologies, #199293-83-9) according to the manufacturer's instructions. After this, the antibody was purified using a PD-10 column (GE Healthcare, #383420). IgE from Biomol GmbH was labeled with NSPSA-NHS in the same manner.

1b. Preparation of Allergen Dilutions:

T2 elder pollen extract (Squarix, #T-4402), t3 birch pollen extract (Squarix, #T-4400) and t4 hazel pollen extract (Squarix, #T-4404) were diluted in concentrations of 10 µg/ml, 1 µg/ml, 100 ng/ml, 10 ng/ml, and 1 ng/ml in dilution buffer (1x Hank's Balanced Salt Solution (Thermo Fisher Scientific #14065056), 40 mM HEPES, pH 7.4). Dilution buffer was used as a negative control. fMLP (Sigma, #F3506-5MG) in a concentration of $10^{-6}$ M and anti-FcεRI antibody (Klon AER-37, ebioscience, #14-5899-82) in a concentration of 100 ng/ml were used as positive controls. Moreover, apple extract (Squarix #F-2327), timothy grass pollen extract (Squarix, #G-5501), e94 (purified according to Rogers et al. (1993), Recombinant Fel d.I: Expression, purification, IgE binding and reaction with cat-allergic human T cells., Molecular Immunology, 30 Apr. 2010 (6), 559-568), mugwort pollen extract (Squarix #W-3400), dog hair extract (Squarix #E-6617), wasp venom extract (Squarix #I7804), i209 (purified according to Seismann et al., 2010, Clinical and Molecular Allergy, 8:7), dandelion pollen extract (Squarix #W-3404) and hazelnut extract (Squarix, #T-4404) were used as antigens.

1c. Stimulation:

50 µl each of peripheral whole blood (heparinized) was mixed in a microtiter plate with 50 µl each of allergen or control dilution and incubated in an incubator for 20 min at 37° C. The reaction was stopped by adding 10 µl of a concentrated EDTA solution (100 mM EDTA in PBS).

2a1. Antibody Incubation:

After this, two antibodies were added to the samples:
1) anti-CD123 biotin (Klon H5C6, Biolegend #353014) in a final concentration of 0.5 µg/ml
2) anti-CD63-NSP-SA (Klon 7G3, BD Bioscience #353014) in a final concentration of 2 µg/ml The samples were mixed and incubated for 10 min at room temperature.

Alternatively, anti-CD63 biotin (Biolegend 353017) and anti-CD63-FITC (Miltenyi 130-100-160) were used.

2a2. Erythrolysis:

Erythrocytes were lysed by adding 100 µl of a saponin-containing lysis buffer (0.14% saponin in PBS) and carrying out incubation for 10 min at RT. After this, the microtiter plate was centrifuged for 5 min at 500 g and the supernatant was removed.

2a3. Bead Incubation:

The respective samples were mixed with 10 µg of strepta-vidin-coated magnetic beads (Sera-Mag SpeedBeads streptavidin-blocked particles, GE-Healthcare, #21152104010350) and incubated for 10 min at RT.

2a4. Washing:

The cells bound to the beads were washed 5× with 300 µl of washing buffer (0.05% Tween, 2 mM EDTA, 150 mM NaCl, 0.05% NaN$_3$) in a plate washer, e.g. the Tecan HydroFlex equipped with an MBS96 magnet.

2a5. Detection:

In the subsequent detection, the NSP-SA acridinium ester on the CD63 antibody was triggered using two solutions (H$_2$O$_2$; 0.1 M HNO$_3$ and 0.25 M NaOH (Chemilumines-cence Detection Reagent Kit, Invitron Ltd., #IV1-001)). The chemiluminescence signal produced (flash luminescence) was detected on a plate luminometer, e.g. the Berthold Centro LB 960, at a wavelength of 425 nm.

2a6. Evaluation:

The strength of basophil activation was calculated based on the increase in the chemiluminescence signal compared to the unstimulated control. A stimulation index (SI) can be calculated based on relative light units (RLU) of the activated sample/RLU of the unstimulated sample. Here, the threshold value to be exceeded depends on the test substance.

2b. Flow Cytometry Measurement:

For flow cytometric determination, after activation with anti-CD123-PE (Miltenyi Biotec, #130-098-894), anti-HLA-DR-PerCPVio700 (Miltenyi Biotec, #130-103-873) and anti-CD63-VioBlue (Miltenyi Biotec, #130-100-154) antibodies, the samples were incubated according to the manufacturer's instructions under protection from light for 15 min at 4° C.

After addition of 1 ml of 1×FACS lysing solution (BD Bioscience, #349202) and incubation for 10 min at RT, the samples were centrifuged at 500 g for 5 min, the supernatant was removed, and the samples were again washed with 500 µl each of washing buffer (PBS without Ca$^{2+}$/Mg$^{2+}$, 0.5% BSA, 2 mM EDTA, 0.05% NaN$_3$). Measurement was carried out on the flow cytometer, e.g. the MACS Quant (Miltenyi Biotec) within 2 h. Cells with a CD123$^+$/HLA-DR$^-$ phenotype were identified as basophils. Basophils were activated when the CD63 signal exceeded a selected threshold value. Total activation of ≥10% was evaluated as positive.

2c. Fluorescence Measurement

The fluorescence of anti-CD63-FITC was measured with a BMG Labtech FLUOstar (485 nm/520 nm) unit.

Results:

The chemiluminescence test (FIG. 1) was evaluated as positive when the signal of the stimulated sample doubled in relation to the control (SI ≥2). In evaluation of the flow cytometric determinations (FIG. 2), all samples showing activation of ≥10% were evaluated as positive. Comparison of the chemiluminescence test with the flow cytometry test shows a good correlation between the results of the two test systems and very good reproducibility. Here, the dynamic measurement range of the chemiluminescence signal is significantly broader than that of the fluorescence signal.

In flow cytometric evaluation, analysis windows must be set for defining the activated and non-activated cell populations (gating) that must be individually adapted for each patient and subjectively set by the respective evaluating party. This possibility of varying evaluation does not exist in the chemiluminescence test, because in the latter test it is only the relationship of the stimulated sample to the control that is constituted. This allows a standardized evaluation that cannot be carried out in this manner in a flow cytometric test. Moreover, significantly higher sample throughput is made possible by the sample preparation in the microtiter plate format, the rapid measurement and the simple evaluation.

This test also showed that the use of chemiluminescence as a detection system provides a decisive advantage: the basophils and further cells show only very little autochemi-luminescence. Absolute purity of the target cells in measurement is therefore not required.

In contrast, dead cells and granulocytes in particular possess a high degree of auto fluorescence, which would cause overlapping of the desired signal in flow cytometry and thus requires corresponding gating. In use of the CD123 biotin antibody for purification of the basophils, the samples have a low content in particular of dendritic cells, which also express CD123 on the surface. However, as these cells do not express CD63, the detected anti-CD63 chemilumines-cence signal is exclusively attributable to the basophils. The measurement itself is not impaired by the presence of other unlabeled cells.

The combination of chemiluminescence as a detection method with the presence of unfractionated whole blood therefore provides a highly sensitive detection method with which a plurality of samples can be processed in parallel with maximum reproducibility and standardizability.

FIGS. 3A-H-10A-J demonstrate with a wide variety of antigens and sample donors that the method according to the invention is widely applicable. In each case, the first figure (e.g. FIGS. 3A-H) shows the same experiment with chemi-luminescence and the following figure (FIGS. 4A-H) with flow cytometry in order to demonstrate comparability. The result is that this comparability is surprisingly high. The method according to the invention can therefore replace flow cytometry.

FIGS. 11A-C show a direct comparison of the three detection methods chemiluminescence, fluorescence and flow cytometry. It can be clearly seen that chemiluminescence roughly corresponds to flow cytometry in sensitivity and is significantly more suitable than fluorescence, thus confirming that the method according to the invention can replace flow cytometry.

Finally, the experiment shown in FIGS. 12A-E demonstrates that the method according to the invention also functions properly when an activation-dependent ligand is used for enrichment and an activation-independent ligand is used for detection rather than vice versa, as was the case in the other experiments. In this case, although the background in chemiluminescence is higher than the signal, the signal can be clearly distinguished from the background.

The invention claimed is:

1. A method for detecting activated basophils, comprising the following steps:
    a) contacting a whole blood sample of a patient that comprises basophils with an allergen in an aqueous solution under conditions that allow activation of the basophils by the allergen, wherein the whole blood sample is at least 20 percent by volume of the mixture comprising the whole blood sample and the aqueous solution,
    b) enriching the basophils from step a) without use of a flow cytometer by binding the basophils to
        (1) a first antibody that binds a first cell surface polypeptide characteristic of activated basophils, or
        (2) a first antibody that binds a first basophil cell surface polypeptide independent of activation status of basophils, and
    c) detecting activated basophils in the enriched basophil from step b) by chemiluminescence, wherein
        (1) if step b) (1) is performed, step c) is carried out by detecting the activated basophils using a second antibody that binds a second cell surface polypeptide characteristic of activated basophils or a second antibody that binds a second basophil cell surface polypeptide independent of activation status of basophils, or
        (2) if step b) (2) is performed, step c) is carried out by detecting the activated basophils using a second antibody that binds a second cell surface polypeptide characteristic of activated basophils, wherein either the first antibody or the second antibody is labeled with a label capable of chemiluminescence or the activated basophils are detected by a secondary antibody with a label capable of chemiluminescence binding to the first antibody or the second antibody.

2. The method of claim 1, wherein the whole blood sample is an unprocessed whole blood sample.

3. The method of claim 1, wherein in step a), the whole blood sample is at least 40 percent by volume of the mixture comprising the whole blood sample and the aqueous solution.

4. The method of claim 1, further comprising the step of stopping the activation of the basophils before step b).

5. The method of claim 1, wherein steps b) (2) and c) (2) are performed.

6. The method of claim 5, wherein the first antibody is a monoclonal antibody against the first basophil cell surface polypeptide independent of activation status of basophils.

7. The method of claim 1, wherein in step b), the basophils are immobilized.

8. The method of claim 7, wherein the basophils are immobilized on a bead.

9. The method of claim 7, wherein the basophils are washed after immobilization.

10. The method of claim 1, wherein in step b), erythrocytes of the whole blood sample are lysed and removed.

11. The method of claim 10, wherein the basophils are immobilized in step b), and wherein the erythrocytes are removed by centrifugation before the basophils are immobilized.

12. The method of claim 1, wherein the second antibody comprises a group capable of chemiluminescence.

13. The method of claim 12, wherein the second antibody is a monoclonal antibody that binds to a secondary antibody with a label capable of chemiluminescence.

14. The method of claim 1, wherein steps a), b) and c) are carried out in a well of a microtiter plate.

15. A method for treating an allergy, comprising:
    (1) detecting activated basophils according to claim 1, and
    (2) if activated basophils are detected, administering to the patient an effective amount of a therapeutic agent or treatment for type I hypersensitivity.

16. The method of claim 15, wherein the therapeutic agent or treatment comprises an antihistamine, a mast cell stabilizer, a steroid, cyclosporine, adrenaline, or immunotherapy.

17. The method of claim 1, wherein steps b) (1) and c) (1) are performed.

18. A method for screening candidate active ingredients for treating allergy to an allergen, comprising:
    (1) detecting activated basophils according to claim 1 in a patient,
    (2) a) contacting a whole blood sample of the patient with a candidate active ingredient to generate a treated whole blood sample, and
        b) detecting activated basophils according to claim 1 using the treated whole blood sample, and
    (3) comparing the level of activated basophils of step (1) with the level of activated basophils of step (2), wherein the candidate active ingredient is effective in treating an allergy caused by the allergen if the level of activated basophils of step (2) is lower than the level of activated basophils of step (1).

19. A method for detecting activated basophils, comprising:
    a) enriching basophils from a whole blood sample of a patient without use of a flow cytometer by binding the basophils to a first antibody that binds a basophil cell surface polypeptide independent of activation status of basophils,
    b) contacting the enriched basophils from step a) with an allergen in an aqueous solution in the presence of whole blood under conditions that allow activation of the basophils by the allergen, wherein the whole blood is at least 20 percent by volume of the mixture comprising the whole blood and the aqueous solution, and
    c) detecting activated basophils in the mixture of step b) by chemiluminescence using a second antibody that binds a cell surface polypeptide characteristic of activated basophils, wherein either the first antibody or the second antibody is labeled with a label capable of chemiluminescence or the activated basophils are detected by a secondary antibody with a label capable of chemiluminescence binding to the first antibody or the second antibody.

* * * * *